US012721910B2

(12) United States Patent
Jermy

(10) Patent No.: US 12,721,910 B2
(45) Date of Patent: Sep. 1, 2026

(54) METHOD FOR TREATING CANCEROUS TISSUE WITH A NANOTHERAPEUTIC

(71) Applicant: Imam Abdulrahman Bin Faisal University, Dammam (SA)

(72) Inventor: B. Rabindran Jermy, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 521 days.

(21) Appl. No.: 18/363,952

(22) Filed: Aug. 2, 2023

(65) Prior Publication Data

US 2023/0381346 A1 Nov. 30, 2023

Related U.S. Application Data

(62) Division of application No. 16/295,729, filed on Mar. 7, 2019, now Pat. No. 11,759,534.

(51) Int. Cl.

| | |
|---|---|
| ***A61K 49/00*** | (2006.01) |
| ***A61K 9/50*** | (2006.01) |
| ***A61K 9/51*** | (2006.01) |
| ***A61K 33/243*** | (2019.01) |
| ***A61K 49/18*** | (2006.01) |
| ***A61P 35/00*** | (2006.01) |
| ***B01J 21/08*** | (2006.01) |
| ***B01J 29/00*** | (2006.01) |
| ***B01J 29/03*** | (2006.01) |
| ***B01J 29/035*** | (2006.01) |
| ***C07C 5/48*** | (2006.01) |

(52) U.S. Cl.

CPC ........ *A61K 49/0093* (2013.01); *A61K 9/5015* (2013.01); *A61K 9/5115* (2013.01); *A61K 9/5192* (2013.01); *A61K 33/243* (2019.01); *A61K 49/0041* (2013.01); *A61K 49/1824* (2013.01); *A61P 35/00* (2018.01); *B01J 21/08* (2013.01); *B01J 29/005* (2013.01); *B01J 29/0333* (2013.01); *B01J 29/0341* (2013.01); *B01J 29/0356* (2013.01); *B01J 29/0358* (2013.01); *C07C 5/48* (2013.01); *B01J 2235/00* (2024.01); *B01J 2235/15* (2024.01); *C07C 2529/40* (2013.01); *C07C 2529/70* (2013.01); *C07C 2529/80* (2013.01)

(58) Field of Classification Search

None

See application file for complete search history.

(56) References Cited

U.S. PATENT DOCUMENTS

| | | | |
|---|---|---|---|
| 5,260,501 A | 11/1993 | Bhore et al. | |
| 6,187,983 B1 | 2/2001 | Sun | |
| 6,497,857 B1 | 12/2002 | Cheng et al. | |
| 8,932,974 B2 | 1/2015 | Garcia-Martinez | |
| 2008/0050308 A1 | 2/2008 | Vermeiren | |
| 2012/0024776 A1 | 2/2012 | Garcia-Martinez | |
| 2013/0165315 A1 | 6/2013 | Al-Khattaf et al. | |
| 2020/0282081 A1 * | 9/2020 | Jermy .................. | A61K 9/0009 |

FOREIGN PATENT DOCUMENTS

| | | |
|---|---|---|
| CN | 104058421 A | 9/2014 |
| CN | 105921148 A | 9/2016 |

OTHER PUBLICATIONS

Baker, Sharyn D., Alex Sparreboom, and Jaap Verweij. "Clinical pharmacokinetics of docetaxel: recent developments." Clinical pharmacokinetics 45.3 (2006): 235-252. (Year: 2006).*

Y. Sang et al., "HZSM-5/MCM-41 composite molecular sieves for the catalytic cracking of endothermic hydrocarbon fuels: nano-ZSM-5 zeolites as the source" Journal of Nanoparticle Research, vol. 16, 2014, pp. 1-11.

G. Li, et al., "Exploring suitable ZSM-5/MCM-41 zeolites for catalytic cracking of n-dodecane: Effect of initial particle size and Si/Al ratio" Chinese Journal of Chemical Engineering, vol. 23, Issue 10, 2015, pp. 1655-1661.

Huiyong, C., et al., "Experimental and molecular simulation studies of a ZSM-5-MCM-41 micro-mesoporous molecular sieve"; Microporous and Mesoporous Materials; pp. 396-402 (Year: 2009).

Wang, Y., et al., "Mesoporous silica nanoparticles in drug delivery and biomedical applications", Nanomedicine, pp. 313-327 (Year: 2015).

Simonetti, S., et al., "Modeling of CN-functionalized silica as vehicle for delivery of the chemotherapeutic agent: cisplatin", Appl. Phys. A., pp. 63-68 (Year: 2012).

Agundez, J., et al., "Activity Enhancement of Mesoporous Aluminosilicates Synthesized From ZSM-5 Precursors", Studies in Surface Science and Catalysis, pp. 2907-2914 (Year: 2004).

* cited by examiner

*Primary Examiner* — Michael G. Hartley
*Assistant Examiner* — Jong Hwan Baek
(74) *Attorney, Agent, or Firm* — Oblon, McClelland, Maier & Neustadt, L.L.P.

(57) ABSTRACT

A nanotherapeutic supported by a hierarchical silica composite with dual imaging capability (e.g. fluorescence and magnetic resonance imaging), a method of preparing the nanotherapeutic, and a method of treating cancer. Also disclosed is a method of oxidatively dehydrogenating ethane using a catalytic system supported by a hierarchical silica composite.

10 Claims, 8 Drawing Sheets

NiO (active site for reactant)

Crystalline of $\alpha/\beta$–$Bi_2O_3$ (active as oxygen supplier)

Crystalline of $NiO/Bi_2O_3$ (active as oxygen supplier)

NiO (Active site for reactant)

Semi Crystalline $Bi_2O_3$ (active as oxygen supplier)

60.0
50.0
40.0
30.0
20.0
10.0
0.0

$C_2H_6$ conversion (%)

400 450 500 550 600 650

Temperature (°C)

20wt%Ni/g-alumina (850 °C; 2 h)
20wt%Ni/g-alumina (1000 °C; 2 h)
20wt%Ni/g-alumina (560 °C; 2 h)

METHOD FOR TREATING CANCEROUS TISSUE WITH A NANOTHERAPEUTIC

CROSS-REFERENCE TO RELATED APPLICATIONS

The present application is a Divisional of U.S. application Ser. No. 16/295,729, now allowed, having a filing date of Mar. 7, 2019.

BACKGROUND OF THE INVENTION

Technical Field

The present invention relates to a hybrid nanotherapeutic that includes a hierarchical silica composite loaded with an antitumor agent and imaging agents. The present invention further relates to a method of oxidative dehydrogenation using a catalyst comprising nickel and other cation dopants including niobium, aluminum, titanium, tantalum, bismuth, and/or oxides thereof impregnated on a hierarchical silica composite.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Structured silica/metal oxide mesosilicates (J. S. Beck, J. C. Vartuli, W. J. Roth, M. E. Leonowicz, C. T. Kresge, K. D. Schmitt, C. T. W. Chu, D. H. Olson, E. W. Sheppard, S. B. B. McCullen, J. B. Higgins, J. L. Schlenker, *J. Am. Chem. Soc.* 1992, 114, 10834; and Q. S. Huo, D. I. Margolese, U. Ciesla, P. Y. Feng, T. E. Gier, P. Sieger, R. Leon, P. M. Petroff, F. Schuth, G. D. Stucky, *Nature* 1994, 368, 317, each incorporated herein by reference in their entirety) have gained prominent uses in different domains, such as catalysis, drug delivery, and gas adsorption. Though several designed mesoporous materials are reported, they lack real world industrial applications due to their amorphous nature, and poor steam and hydrothermal stability. Combining the advantages of microporous zeolites and mesoporous materials, mesoporous zeolites are considered to be one of the most effective materials to enhance catalyst stability and pore approachability of nanopores. For instance, hierarchical micro/mesoporous zeolites are reported to show remarkable thermal and hydrothermal stability, tunable acidity, enhanced adsorption and diffusion efficiency. The improvement in stability is a result of the presence of nanozeolitic seeds (primary or secondary zeolitic building units) in the synthesis gel which increases the framework crystallinity.

In addition to being used as the monomer of polyethylene (PE), ethylene is a common precursor to other commercial monomers, e.g. vinyl chloride and styrene, leading to synthetic polymers, e.g. polyvinyl chloride (PVC) and polystyrene (PS). Ethylene production strongly relies on steam cracking. Alternatively, ethylene can be produced by dehydrogenation of ethane under catalytic cracking conditions. The endothermic process works under reduced partial pressure to reduce the formation of by-products and coke.

Though conventional dehydrogenation catalysts are robust and active, they still have some drawbacks. For instance, potassium migration tends to occur with longer catalyst life cycles due to water condensation and coolant effects. The presence of toxic chromium is also detrimental to humans and the environment. The quest to find new robust catalysts with high surface area, and uniform pore size distribution that can stabilize the active state of nickel/iron/cobalt species without the promoter (e.g. potassium) and toxic metal oxides (e.g. chromium oxide) is much needed.

Oxidative dehydrogenation has significant advantages over conventional dehydrogenation as the process is not limited by thermodynamic equilibrium, can be carried out at lower temperatures, and catalytic site deactivation is reduced as a result of the presence of oxygen. Nickel oxide based catalysts have been shown to be effective in oxidative dehydrogenation of ethane. In recent years, an increased interest is shown in using nickel oxide supported systems for mixed oxide catalysts in oxidative dehydrogenation. In particular, Ni/Alumina based catalyst is much preferred due to presence of nickel active centers for reactant activation. Dopants such as tantalum have been demonstrated to alter the NiO lattice and thereby influence the amount of product distribution selectivity in ethane oxidative dehydrogenation. The presence of higher valence cation dopants such as $Nb^{5+}$, $Al^{3+}$, $Ti^{4+}$, and $Ta^{5+}$ was reported to subdue the unselective deeper oxidation by controlling the higher oxidation state of nickel species (Heracleous E, Lemonidou A A *J. Catal.* 2010, 270, 67, incorporated herein by reference). However, in oxidative dehydrogenation, selective oxidation of ethane to ethylene is not a simple process. For instance, lower temperature is sufficient for the dehydrogenated product (i.e. ethylene) to react rapidly with oxygen to form stable combustion products like carbon dioxide and water (I.-C. Marcua, I. Sandulescu, J.-M. M. Millet *J. Mol. Catal. A: Chem.,* 2003, 203, 241, incorporated herein by reference). Therefore, an alternative catalyst with controlled oxidative dehydrogenation activity is needed to overcome this limitation. Previous work (B. Rabindran Jermy, B. P. Ajayi, B. A. Abussaud, S. Asaoka, S. Al-Khattaf, *J. of Mol. Catal. A: Chem.* 2015, 400, 121; and B. Rabindran Jermy, S. Asaoka, S. Al-Khattaf, *Catal. Sci. Technol.,* 2015, 5, 4622, each incorporated herein by reference in their entirety) has demonstrated the effectiveness of nickel catalysts supported over alumina and silicalite on oxidative dehydrogenation of ethane to ethylene. See FIGS. 3-11.

Nanotherapeutics have broadened the scope of effective and efficient treatment on deadly diseases such as cancer, diabetic and other metabolic disorders. Biocompatible nanosilica carriers have been tested through various approaches in medicine research for target oriented drug therapy. However, so far only 5% of the drug reaches the tumors with a nanosilica carrier. In addition, the detection of the tumor is often limited by the sensitivity and resolution of a single imaging system.

Magnetic resonance imaging (MRI) is a medical imaging technique used in radiology to generate pictures of the anatomy and physiological processes of a body in both health and disease. The advancement of MRI technology also provides a tool to non-invasively and continuously monitor a drug delivery system with a contrasting agent. Magnetic resonance moieties such as Gadolinium and iron oxides are often administered as contrasting agents to improve the visibility of magnetic resonance imaging (MRI). Magnetic nanosilicas have been used as new transfecting agents (F. Scherer, M. Anton, U. Schillinger, J. Henkel, C. Bergemann, A. Kruger, B. Gansbacher, C. Plank, *Gene Ther.* 2002, 9, 102, incorporated herein by reference), and immunoassay (B. Q. Sun, W. Z. Xie, G. S. Yi, D. P. Chen, Y. X. Zhou, J. Cheng, *J. Immunol. Method.* 2001, 249, 85, incorporated herein by reference). A magnetic nanosilica drug carrier responds to external magnetic field, thereby directs drug delivery and facilitates bioimaging. Furthermore, developing a therapeutic nanosilica carrier with dual imaging modality will be of great significance considering complementary detection channels and enhanced imaging sensitivity.

However, developing suitable pore sized magnetic drug carriers for certain drug molecules coupled with another imaging agent, e.g. a fluorescence dye, in a single entity is cumbersome and challenging. In order to address this need a suitable solid support material is required. Mesoporous silicas such as hexagonal MCM-41, SBA-15, and cubic SBA-16, MCM-18, have been reported to function as drug delivery agents under in vitro (I. I. Slowing, B. G. Trewyn, S. Giri, V. S. Y. Lin, *Adv. Funct. Mater.* 2007, 17, 1225, incorporated herein by reference) and in vivo studies (C. H. Lee, S. H. Cheng, Y. J. Wang, Y. C. Chen, N. T. Chen, J. Souris, C. T. Chen, C. Y. Mou, C. S. Yang, L. W. Lo, *Adv. Funct. Mater.* 2009. 19, 215, incorporated herein by reference). However, a nanosilica carrier with dual imaging capability, which possesses various advantages, e.g. 3D porous networks, extensive diffusional accesses, surface functionalization capabilities, and potential modifications to mesoporous form, has not yet been explored as a drug carrier.

In view of the forgoing, one objective of the present invention is to provide an antitumor nanotherapeutic supported by a hierarchical silica composite with dual imaging capability, and a method of oxidatively dehydrogenating ethane using a catalytic system supported by a hierarchical silica composite.

BRIEF SUMMARY OF THE INVENTION

According to a first aspect, the present disclosure relates to a nanotherapeutic having an antitumor agent, at least one imaging agent selected from the group consisting of a fluorophore and a magnetic resonance imaging moiety, a hierarchical silica composite as a support material, and a silane coating that coats at least a portion of a surface of the hierarchical silica composite. The hierarchical silica composite includes a stereoregular MCM-41 ordered arrangement of uniformly-sized mesopores with diameters in a range of 2-50 nm and mesopore walls having a thickness of about 1 to about 5 nm, a stereoregular ZSM-5 silicalite ordered arrangement of uniformly-sized micropores with diameters of less than 2 nm located within the mesopore walls.

In some embodiments of the nanotherapeutic, the hierarchical silica composite has a silicon to aluminum molar ratio in a range of 1,000:1 to 3,000:1.

In some embodiments of the nanotherapeutic, the mesopores have a pore volume in a range of 0.5-1.5 $cm^3/g$ and a surface area in a range of 800-1,600 $m^2/g$.

In some embodiments of the nanotherapeutic, the antitumor agent is cisplatin.

In some embodiments of the nanotherapeutic, wherein the fluorophore is present, and wherein the fluorophore is rhodamine B isothiocyanate.

In some embodiments of the nanotherapeutic, wherein the magnetic resonance imaging moiety is present, and wherein the magnetic resonance imaging moiety is iron and/or an oxide thereof.

According to another aspect, the present disclosure relates to a method of preparing the nanotherapeutic, wherein the fluorophore is present as the imaging agent. The preparation method involves (i) treating the hierarchical silica composite with a silanization agent to form a silane coated hierarchical silica composite, (ii) mixing the silane coated hierarchical silica composite with a solution of the fluorophore to form a fluorescent hierarchical silica composite, (iii) mixing the fluorescent hierarchical silica composite with a solution of the antitumor agent forms the nanotherapeutic.

According to another aspect, the present disclosure relates to a method of preparing the nanotherapeutic, wherein the magnetic resonance imaging moiety is present as the imaging agent. The preparation method involves (i) incorporating the magnetic resonance imaging moiety into the hierarchical silica composite by a method selected from the group consisting of wet impregnation, isomorphous substitution, and enforced impregnation, to form a magnetic hierarchical silica composite, (ii) treating the magnetic hierarchical silica composite at 500-600° C. for 8-16 hours to form a calcined magnetic hierarchical silica composite, (iii) treating the calcined magnetic hierarchical silica composite with a silanization agent to form a silane coated hierarchical silica composite, (iv) mixing the silane coated hierarchical silica composite with a solution of the antitumor agent forms the nanotherapeutic.

According to another aspect, the present disclosure relates to a method of preparing the nanotherapeutic, wherein the fluorophore and the magnetic resonance imaging moiety are present as the imaging agent. The preparation method involves (i) incorporating the magnetic resonance imaging moiety into the hierarchical silica composite by a method selected from the group consisting of wet impregnation, isomorphous substitution, and enforced impregnation, to form a magnetic hierarchical silica composite, (ii) treating the magnetic hierarchical silica composite at 500-600° C. for 8-16 hours to form a calcined magnetic hierarchical silica composite, (iii) treating the calcined magnetic hierarchical silica composite with a silanization agent to form a silane coated hierarchical silica composite, (iv) mixing the silane coated hierarchical silica composite with a solution of the fluorophore to form a fluorescent hierarchical silica composite, (v) mixing the fluorescent hierarchical silica composite with a solution of the antitumor agent forms the nanotherapeutic.

According to another aspect, the present disclosure relates to a method of treating a cancerous tissue located in a subject in need of treatment for cancer. The treatment method includes (i) administering a therapeutically effective amount of the nanotherapeutic to the subject, (ii) imaging a location of the nanotherapeutic relative to the cancerous tissue by illuminating the cancerous tissue at an electromagnetic wavelength and detecting a fluorescence signal, and/or applying an external magnetic field to the subject for magnetic resonance imaging.

In some embodiments of the method, wherein the fluorophore is present as the imaging agent, the location of the nanotherapeutic is imaged by the illuminating.

In some embodiments of the method, wherein the magnetic resonance imaging moiety is present as the imaging agent, the location of the nanotherapeutic is imaged by the applying.

According to another aspect, the present disclosure relates to a method of oxidatively dehydrogenating an alkane to form an olefin. The oxidative dehydrogenation method involves contacting the alkane with a catalyst, an oxidant, and an inert gas in a reactor to oxidatively dehydrogenate the alkane to the olefin. The catalyst includes a hierarchical silica composite and an active catalytic material impregnated on the hierarchical silica composite. The active catalytic material has nickel and/or nickel oxide, and at least one cation dopant selected from the group consisting of $Nb^{5+}$, $Al^{3+}$, $Ti^{4+}$, $Ta^{5+}$, $Bi^{5+}$, and/or oxides thereof.

In some embodiments of the method, the hierarchical silica composite includes a stereoregular MCM-41 ordered arrangement of uniformly-sized mesopores with diameters in a range of 2-50 nm and mesopore walls having a thickness of about 1 to about 5 nm, and a stereoregular ZSM-5 silicalite ordered arrangement of uniformly-sized micropores with diameters of less than 2 nm located within the mesopore walls.

In some embodiments of the method, the alkane is contacted with the catalyst, the oxidant and the inert gas at a pressure of 70-130 kPa, and a temperature of 450-700° C.

In a further embodiment, the method involves flowing the inert gas through the reactor at a flow rate of 50-150 mL $min^{-1}$, and flowing the alkane through the reactor at a flow rate of 0.5-1.0 mmol $min^{-1}$.

In some embodiments, the method further involves pretreating the catalyst with an inert gas at an inert gas flow rate of 50-150 mL $min^{-1}$ and a temperature of 450-700° C. for 0.5-2 hours.

In some embodiments of the method, the oxidant is $O_2$ and/or $CO_2$, and the inert gas is He.

In some embodiments of the method, the alkane has ethane, and the olefin has ethylene.

According to another aspect, the present disclosure relates to an oxidative dehydrogenation catalyst having a hierarchical silica composite and an active catalytic material impregnated on the hierarchical silica composite. The hierarchical silica composite includes a stereoregular MCM-41 ordered arrangement of uniformly-sized mesopores with diameters in a range of 2-50 nm and mesopore walls having a thickness of about 1 to about 5 nm, and a stereoregular ZSM-5 silicalite ordered arrangement of uniformly-sized micropores with diameters of less than 2 nm located within the mesopore walls. The active catalytic material includes nickel and/or nickel oxide, and at least one cation dopant selected from the group consisting of $Nb^{5+}$, $Al^{3+}$, $Ti^{4+}$, $Ta^{5+}$, and $Bi^{5+}$ and/or oxides thereof.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
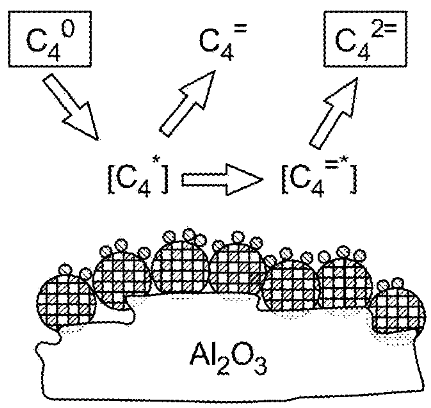
FIG. 1A shows the hierarchical nanoparticle cohabitation catalyst system of $NiO—Bi_2O_3$ with $Al_2O_3$ as a support for oxidative dehydrogenation of n-butane ($C_4^0$) to butadiene ($C_4^2$).
Figure 1B:
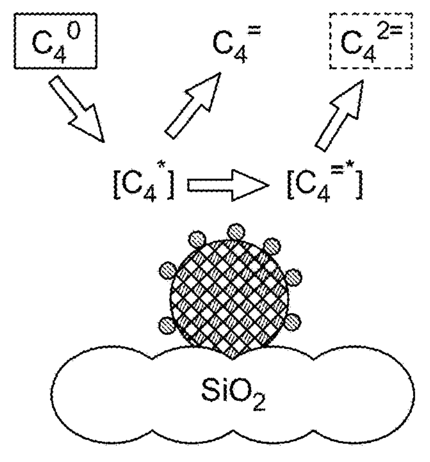
FIG. 1B shows the hierarchical nanoparticle cohabitation catalyst system of $NiO—Bi_2O_3$ with $SiO_2$ as a support for oxidative dehydrogenation of n-butane ($C_4^0$) to butadiene ($C_4^2$).
Figure 1C:
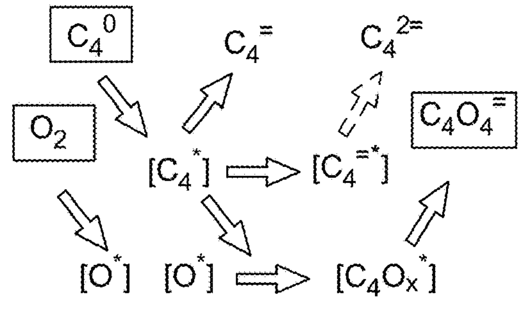
FIG. 1C shows the hierarchical nanoparticle cohabitation catalyst system of $NiO—Bi_2O_3$ with $ZrO_2$ as a support for oxidative dehydrogenation of n-butane ($C_4^0$) to butadiene ($C_4^{2=}$)
Figure 1C:
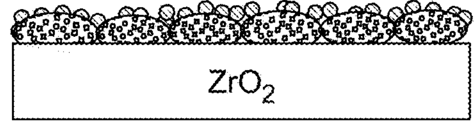
Figure 2A:
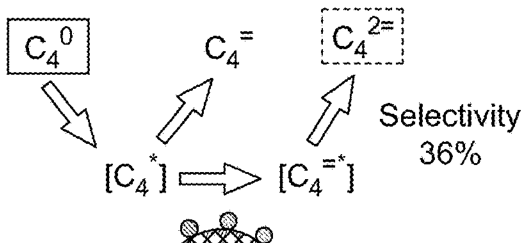
FIG. 2A shows 36% selectivity of oxidative dehydrogenation of n-butane ($C_4^0$) to butadiene ($C_4^{2=}$) using hierarchical nanoparticle cohabitation catalyst of $NiO—Bi_2O_3$ with $SiO_2$ gel as a support.
Figure 2A:
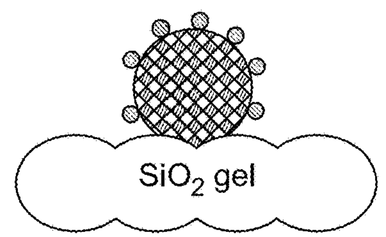
Figure 2B:
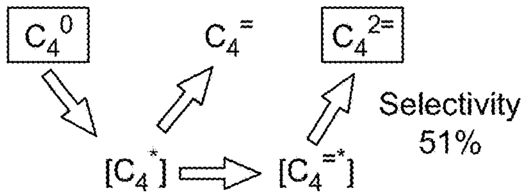
FIG. 2B shows 51% selectivity of oxidative dehydrogenation of n-butane ($C_4^0$) to butadiene ($C_4^{2=}$) using hierarchical nanoparticle cohabitation catalyst of $NiO—Bi_2O_3$ with formed $SiO_2$ as a support.
Figure 2B:
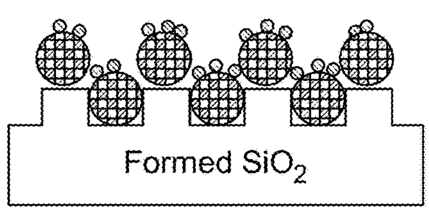
Figure 2C:
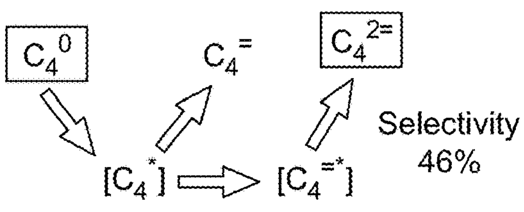
FIG. 2C shows 46% selectivity of oxidative dehydrogenation of n-butane ($C_4^0$) to butadiene ($C_4^{2=}$) using reverse-hierarchical nanoparticle cohabitation catalyst of $NiO—Bi_2O_3$ with non-structured $SiO_2$ sol as a support.
Figure 2C:
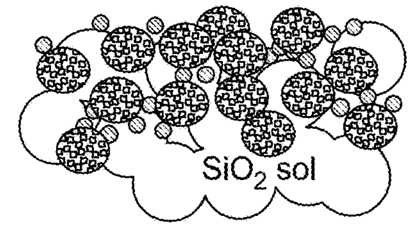
Figure 3:
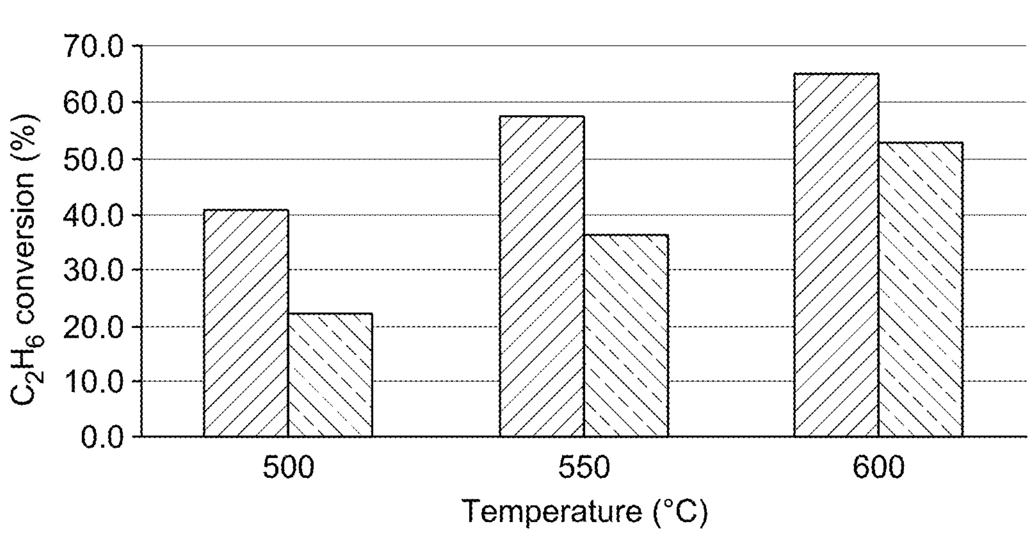
FIG. 3 illustrates oxidative dehydrogenation of ethane to ethylene by showing ethane conversion versus temperature (500, 550, and 600° C.). Catalyst used: 5 & 20 wt. % Ni/γ-alumina calcined at 560° C.; $O_2/C_2$ ratio=2; catalyst amount=0.3 g.
Figure 4:
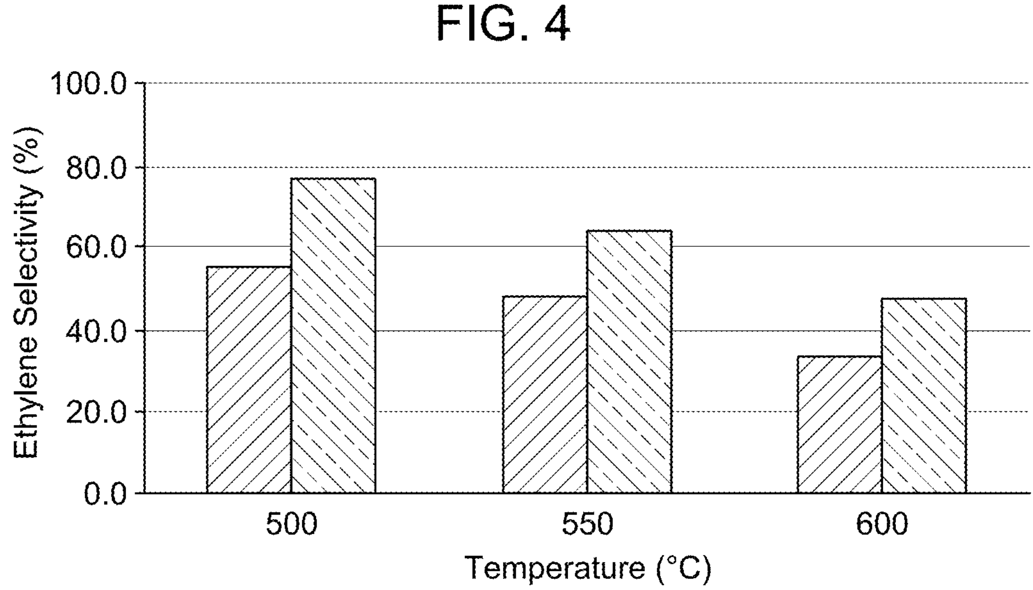
FIG. 4 illustrates oxidative dehydrogenation of ethane to ethylene by showing ethylene selectivity versus ethane conversion (500, 550, and 600° C.). Catalyst used: 5 & 20 wt. % Ni/γ-alumina calcined at 560° C.; $O_2/C_2$ ratio=2; catalyst amount=0.3 g.
Figures 5, 6:
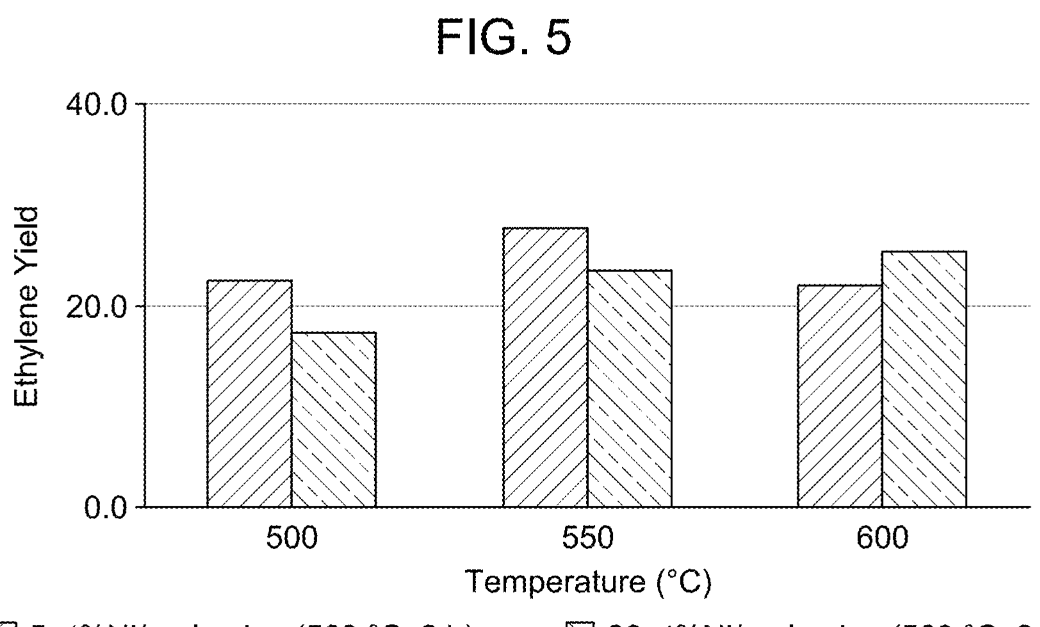
FIG. 5 illustrates oxidative dehydrogenation of ethane to ethylene by showing ethylene yield versus temperature (500, 550, and 600° C.). Catalyst used: 5 & 20 wt. % Ni/γ-alumina calcined at 560° C.; $O_2/C_2$ ratio=2; catalyst amount=0.3 g.
FIG. 6 illustrates oxidative dehydrogenation of ethane to ethylene by showing ethane conversion versus temperature (450, 500, 550, and 600° C.). Catalyst used: 20 wt. % Ni/γ-alumina calcined at 560, 850, and 1000° C.; $O_2/C_2$ ratio=2; catalyst amount=0.3 g.
Figure 7:
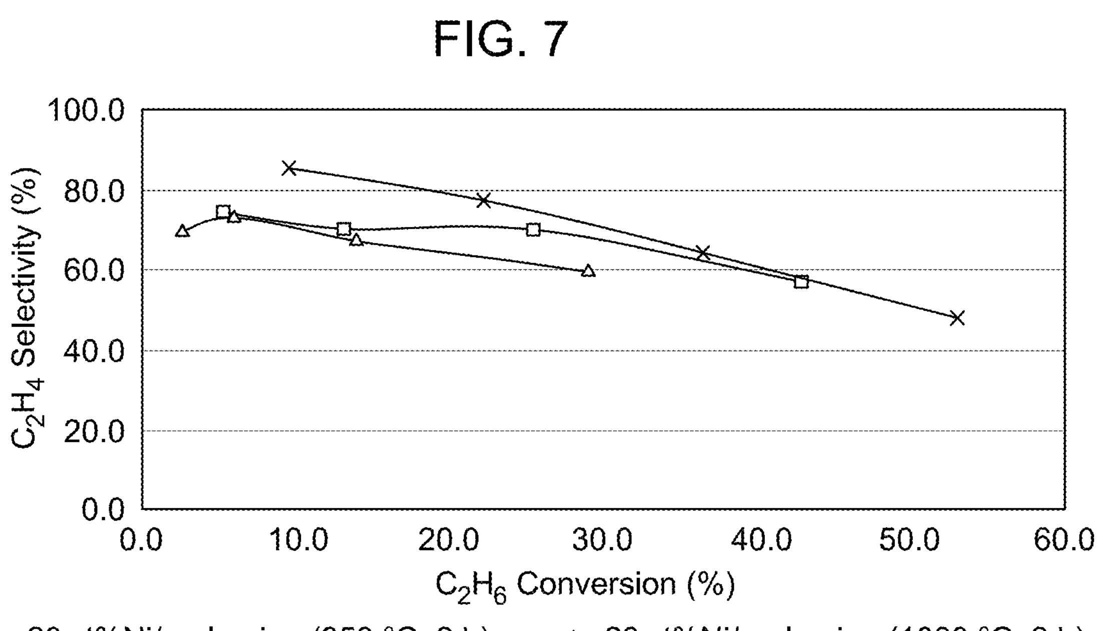
FIG. 7 illustrates oxidative dehydrogenation of ethane to ethylene by showing ethylene selectivity versus ethane conversion. Catalyst used: 20 wt. % Ni/γ-alumina calcined at 560, 850 and 1000° C.; $O_2/C_2$ ratio=2; catalyst amount=0.3 g.
Figure 8:
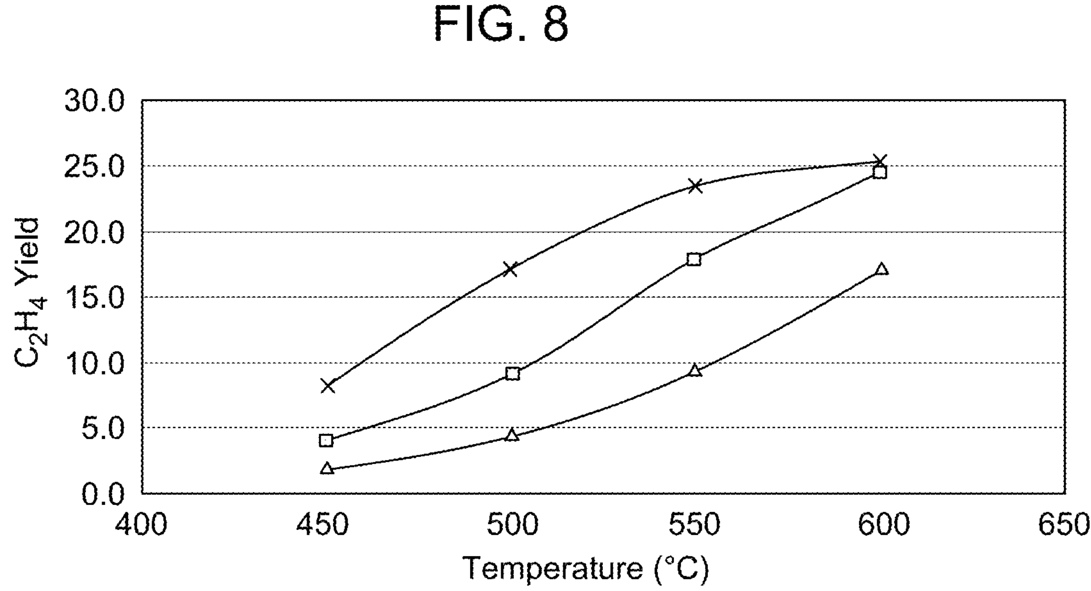
FIG. 8 illustrates oxidative dehydrogenation of ethane to ethylene by showing ethylene yield versus temperatures (450, 500, 550, and 600° C.). Catalyst used: 20 wt. % Ni/γ-alumina calcined at 560, 850 and 1000° C.; $O_2/C_2$ ratio=2; catalyst amount=0.3 g.
Figure 9:
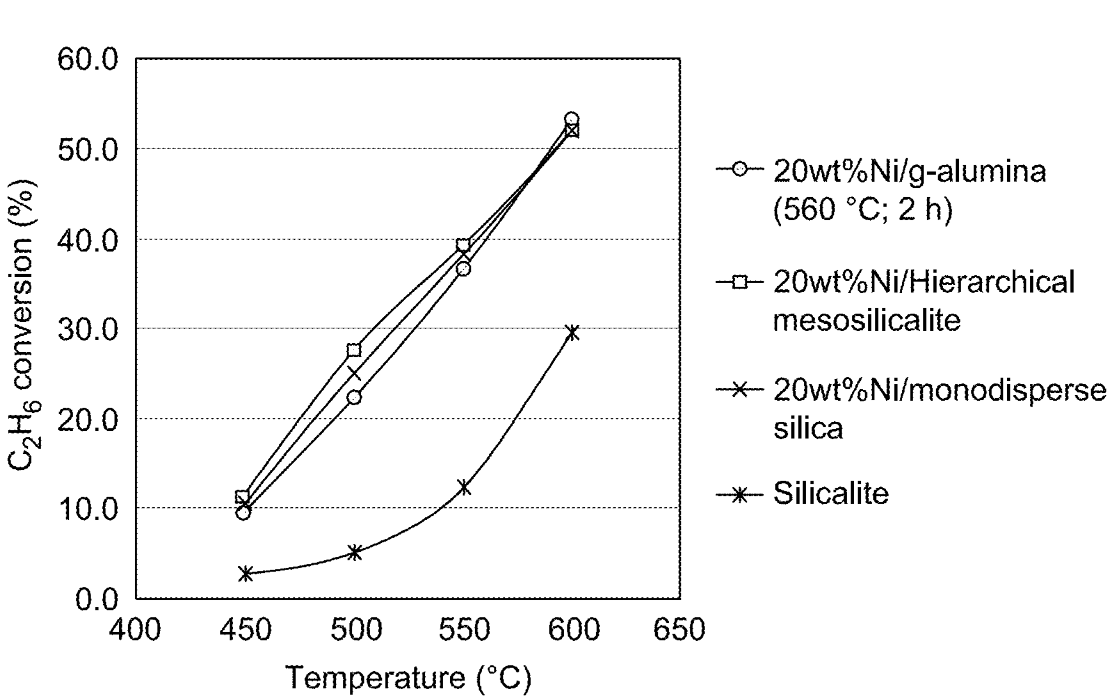
FIG. 9 illustrates oxidative dehydrogenation of ethane to ethylene by showing ethane conversion versus temperature (450, 500, 550, and 600° C.). Catalyst used: 20 wt. % Ni/γ-alumina, 20 wt. % Ni/Hierarchical mesosilicalite, 20 wt. % Ni/monodispersed silica, and 20 wt. % Ni/silicalite calcined at 560° C. for 2 h; $O_2/C_2$ ratio=2; catalyst amount=0.3 g.
Figure 10:
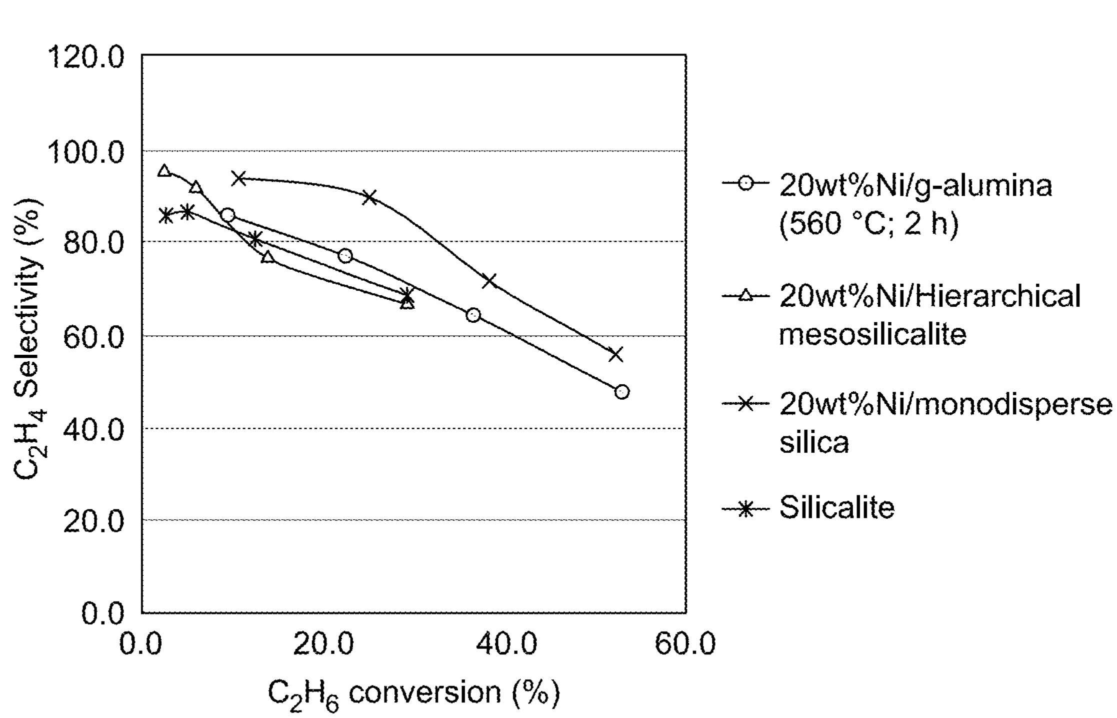
FIG. 10 illustrates oxidative dehydrogenation of ethane to ethylene by showing ethylene selectivity versus ethane conversion (450, 500, 550, 600° C.). Catalyst used: 20 wt. % Ni/γ-alumina, 20 wt. % Ni/Hierarchical mesosilicalite, 20 wt. % Ni/monodispersed silica, and 20 wt. % Ni/silicalite calcined at 560° C. for 2 h; $O_2/C_2$ ratio=2; catalyst amount=0.3 g.
Figure 11:
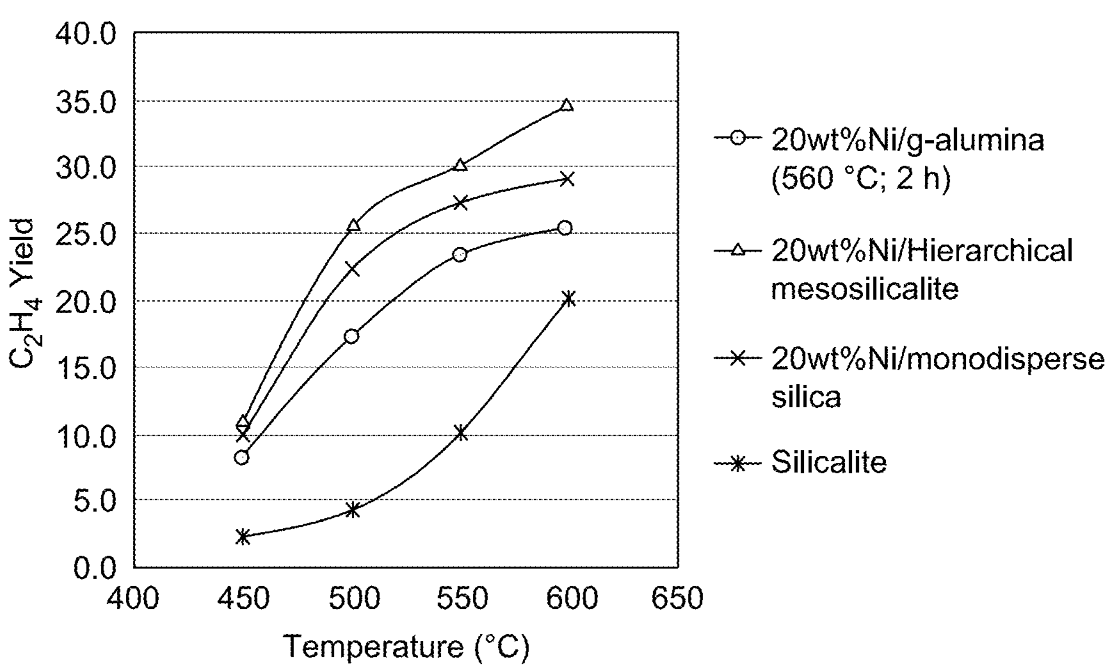
FIG. 11 illustrates oxidative dehydrogenation of ethane to ethylene by showing ethylene yield versus temperatures (450, 500, 550, and 600° C.). Catalyst used: 20 wt. % Ni/γ-alumina, 20 wt. % Ni/Hierarchical mesosilicalite, 20 wt. % Ni/monodispersed silica, and 20 wt. % Ni/silicalite calcined at 560° C. for 2 h; $O_2/C_2$ ratio=2; catalyst amount=0.3 g.
Figure 12:
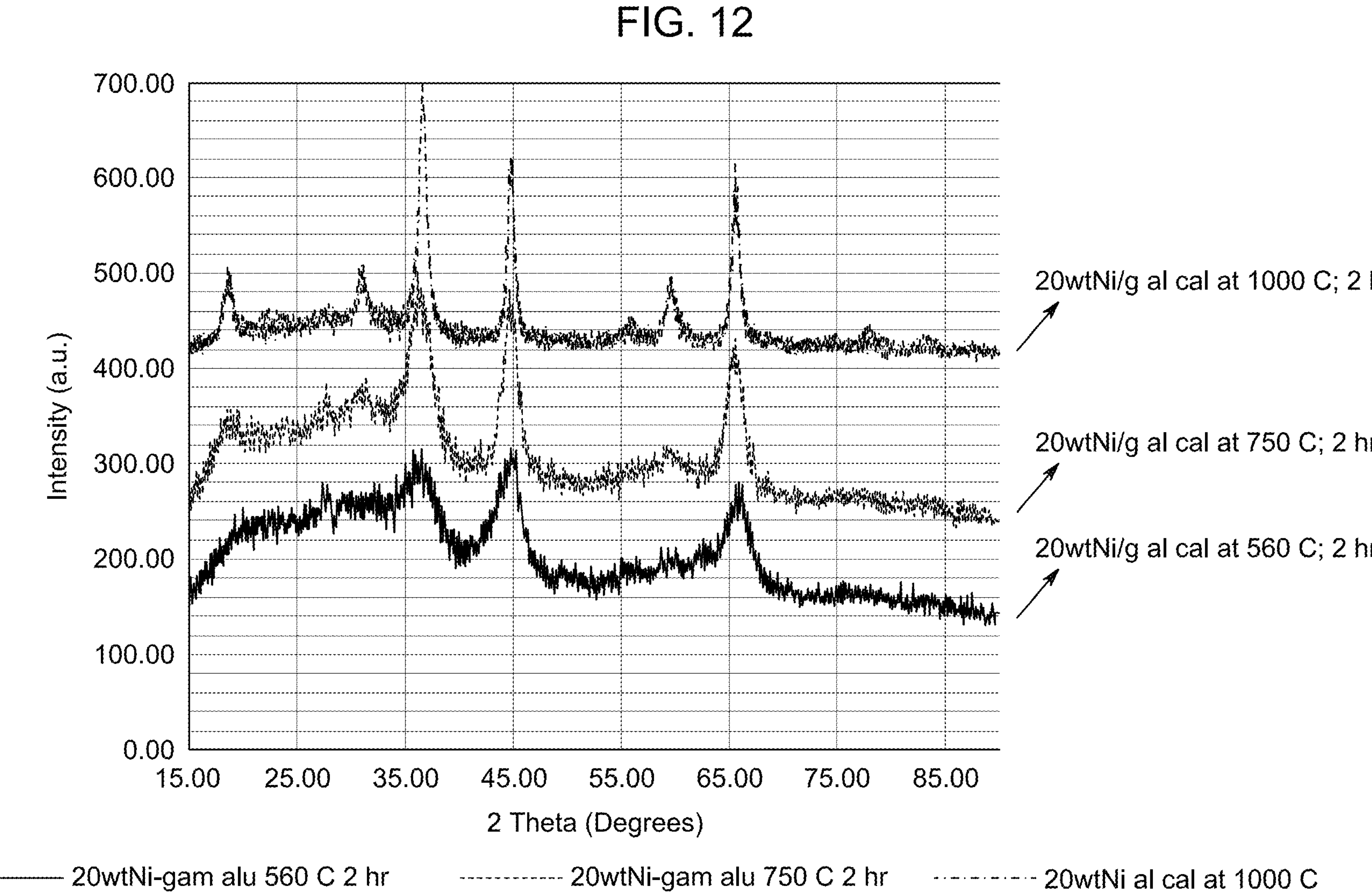
FIG. 12 shows an overlay of XRD profiles of 20 wt. % Ni/γ-alumina calcined at 560, 750, and 1000° C. for 2 h, respectively.

Embodiments of the present disclosure will now be described more fully hereinafter with reference to the accompanying drawings, in which some, but not all embodiments of the disclosure are shown.

As used herein, the term "hierarchical" means a material having pores of two or more different sizes within distinct scale ranges, e.g. within a micropore range, within a mesopore range, and/or within a macropore range. In the context of the present invention, the term "hierarchical silica composite" refers to a porous composite having a structure with pores of different size ranges and comprising aluminosilicates having both micropores and mesopores.

The term "micropore" refers to pores with a diameter less than 2 nm.

The term "mesopore" refers to pores with a diameter between 2 and 50 nm.

The term "macropore" refers to pores with a diameter greater than 50 nm.

According to the first aspect, the present disclosure relates to a nanotherapeutic having an antitumor agent, at least one imaging agent selected from the group consisting of a fluorophore and a magnetic resonance imaging moiety, a hierarchical silica composite, and a silane coating that coats at least a portion of a surface of the hierarchical silica composite. This hybrid nanotherapeutic makes it possible for a sustained and prolonged delivering of anticancer drugs, combined with dual spatiotemporal monitoring of the drug distribution.

In some embodiments, the hierarchical silica composite has a silicon to aluminum molar ratio in a range of 100:1 to 10,000:1, preferably 500:1 to 5,000:1, more preferably 1,000:1 to 3,000:1.

The Brunauer-Emmet-Teller (BET) theory (S. Brunauer, P. H. Emmett, E. Teller, *J. Am. Chem. Soc.* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. In most embodiments, BET surface area and pore volume are measured by gas adsorption analysis, preferably $N_2$ adsorption analysis.

The term "uniformly-sized" used herein refers to a pore size distribution profile having a standard deviation in a range of 1-25%, preferably 1-10%, more preferably 1-5%, still more preferably 1-3%, and most preferably less than 1%. The pore size distribution may be characterized using a method developed by Barrett, Joyner and Halenda (BJH) (E. P. Barrett, L. G. Joyner, P. P. Halenda, *J. Am. Chem. Soc.* 1951, 73, 373-380, incorporated herein by reference) by measuring surface area and pore volume through gas adsorption analysis.

In some embodiments, the hierarchical silica composite includes a stereoregular MCM-41 ordered arrangement of uniformly-sized mesopores with diameters in a range of 2-50 nm, 3-10 nm, or 4-5 nm, and mesopore walls having a thickness of about 1 to about 5 nm, about 2 to about 4 nm, or about 3 to about 4.5 nm, and a stereoregular ZSM-5 silicalite ordered arrangement of micropores with diameters of 0.1-1.99 nm, 0.2-1 nm, or 0.3-0.7 nm located within the mesopore walls.

In some embodiments, the hierarchical silica composite has mesopores with a pore volume of 0.5-1.5 $cm^3/g$, 0.7-1.3 $cm^3/g$, or 0.9-1.1 $cm^3/g$.

In some embodiments, the hierarchical silica composite has mesopores with a surface area of 800-1600 $m^2/g$, 900-1,400 $m^2/g$, or 1,000-1,200 $m^2/g$.

Typically, the amount of the hierarchical silica composite is in the range of 5-90 w.t. %, preferably 15-70 w.t. %, more preferably 25-50 w.t. % relative to the total weight of the nanotherapeutic.

In some embodiments of the nanotherapeutic, the antitumor agent includes, but is not limited to: alkylating antineoplastic agents including cisplatin, busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, methotrexate, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

Cisplatin is widely prescribed in chemotherapy medications for the treatment of ovarian, cervical, testicular, lung, breast, bladder, head and neck cancers. In some embodiments, the antitumor agent preferably includes cisplatin and derivatives, e.g. carboplatin, oxaliplatin, nedaplatin, lobaplatin, heptaplatin, dicycloplatin, other platinum-based antineoplastic drugs, and mixtures thereof.

In some embodiments, the antitumor agent is located inside the mesopores and micropores of the hierarchical silica composite. Preferably, the antitumor agent is located inside the mesopores of the hierarchical silica composite.

Typically, the amount of the antitumor agent is in a range of 0.1-40 w.t. %, preferably 5-30 w.t. %, more preferably 10-20 w.t. % relative to the total weight of the nanotherapeutic.

As used herein, fluorescence is the emission of light by a fluorophore that has absorbed light or other electromagnetic radiation. It is a form of luminescence. Fluorescence occurs when an orbital electron of a molecule, atom, or nanostructure relaxes to its ground state by emitting a photon from an excited singlet state. In most cases, the emitted light has a longer wavelength, and therefore lower energy, than the absorbed radiation in a phenomenon known as the Stokes shift.

In some embodiments of the nanotherapeutic, a fluorophore is present. The fluorophore may include, but is not limited to fluorescein, rhodamine, Texas red, cyanine, indocarbocyanine, merocyanine, squaraine, naphthalene, anthracene, pyrene, acridine, coumarin, oxadiazole, BODIPY® boron-dipyrromethene fluorescent dye, and derivatives thereof.

In some embodiments, the fluorophore has an excitation wavelength at the range of 200-1,500 nm, 300-1,000 nm, 400-800 nm, or 500-700 nm, and an emission wavelength at the range of 200-1,500 nm, 300-1,000 nm, 400-800 nm, or 500-700 nm. In some embodiments, the fluorophore used herein has a Stokes shift of at least about 10 nm, about 20 nm, about 30 nm, about 40 nm, about 50 nm, about 60 nm, about 70 nm, about 80 nm, about 90 nm, or about 100 nm, which is calculated based on the difference between emission and excitation peaks. A large Stokes shift is advantageous as it reduces overlap between the emission profile and background excitation light and thus offers fluorescence images of higher resolution. Preferably, the fluorophore is rhodamine B isothiocyanate having an excitation wavelength at around 540 nm, and an emission band at around 580 nm. Rhodamine B isothiocyanate is intensively used in biology as a staining fluorescent dye with broad applications such as fluorescence microscopy, biomolecular labeling and bioimaging. An effective excitation wavelength of the fluorophore used herein, e.g. Rhodamine B isothiocyanate that is within the visible light region can prevent potential damages to living biological samples.

As used herein, quantum yield (Φ) refers to the fluorescence quantum yield of a fluorophore and gives the efficiency of the fluorescence process. It is defined as the ratio of the number of photons emitted to the number of photons absorbed. The maximum fluorescence quantum yield is 1.0 (100%); wherein each photon absorbed results in a photon emitted. An alternative way to define the quantum yield of fluorescence is by the rate of excited state decay. In some embodiments, the fluorophore used herein has a quantum yield in a range of 0.05-0.9, preferably 0.1-0.8, preferably 0.2-0.7, preferably 0.3-0.6, preferably 0.4-0.5 for its fluorescence emission wavelength at the range of 200-1,500 nm, 300-1,000 nm, 400-800 nm, or 500-700 nm at an excitation wavelength at the range of 200-1,500 nm, 300-1,000 nm, 400-800 nm, or 500-700 nm.

In some embodiments, the fluorophore is located inside the micropores and mesopores, and on the surface of the hierarchical silica composite. Preferably, the fluorophore is located on the surface of the hierarchical silica composite through a chemical bond and/or an electrostatic interaction.

Typically, when present, the amount of the fluorophore is in the range of 0.1-15 w.t. %, preferably 1-10 w.t. %, more preferably 5-7.5 w.t. % relative to the total weight of the nanotherapeutic.

A magnetic resonance imaging moiety may also be present in the nanotherapeutic. Exemplary magnetic resonance imaging moieties include paramagnetic and superparamagnetic species such as manganese(II), manganese-chelate, e.g. Mn-EDTA(ethylenediaminetetraacetic Acid)$^{2-}$, gadolinium(III), gadolinium-chelates, e.g. Gd-DTPA(diethylenetriamine pentaacetic acid)$^{2-}$, and Gd-DOTA(1,4,7,10-tetraazacyclododecane-1,4,7,10-tetraacetic acid)$^{2-}$, iron, iron oxides, e.g. FeO, $Fe_2O_3$ and $Fe_3O_4$, iron platinum species, and the like.

In some embodiments, the magnetic resonance imaging moiety is located within the hierarchical silica composite. Preferably, the magnetic resonance imaging moiety is incorporated into the lattice of the hierarchical silica composite.

Typically, when present, the amount of the magnetic resonance imaging moiety is in the range of 5-35 w.t. %, preferably 10-30 w.t. %, more preferably 15-25 w.t. % relative to the total weight of the nanotherapeutic.

In some embodiments of the nanotherapeutic, the fluorophore and the magnetic resonance imaging moiety are both present in the amounts previously described.

In most embodiments, the nanotherapeutic further includes a silane coating that coats at least a portion of a surface of the hierarchical silica composite. In some embodiments, the silane coating covers at least 20%, at least 40%, preferably at least 50%, more preferably at least 70%, more preferably at least 80%, more preferably at least 90%, or more preferably at least 95% of a total surface area of the hierarchical silica composite. In other embodiments, at least 20%, at least 40%, preferably at least 50%, more preferably at least 70%, more preferably at least 80%, more preferably at least 90%, or more preferably at least 95% of a total number of surface hydroxyl groups on the surface of the hierarchical silica composite are capped by (or reacted with) the silane coating. In some embodiments, the amount of the silane coating is in the range of 1-20 w.t. %, preferably 2.5-15 w.t. %, more preferably 5-10 w.t. % relative to the total weight of the hierarchical silica composite. In some embodiments, the silane coating has a thickness of 10-200 Å, preferably 15-100 Å, more preferably 20-50 Å.

In some embodiments, a surface of the hierarchical silica composite further incorporates different functional groups including, but not limited to polyethylene glycol (PEG), amines, carboxyl groups (e.g. carboxylic acids), and phosphate groups. In some embodiments functional groups are incorporated onto the surface of the hierarchical silica composite by reacting designated functional groups with silanol groups on the surface of the hierarchical silica composite.

In some embodiments, targeting moieties are also attached to the surface of the hierarchical silica composite. Targeting moieties include, but are not limited to, folic acid, sugars, enzymes, antibodies, peptides, and DNA aptamers. In one embodiment, targeting moieties are attached to the surface of the nanotherapeutic through covalent bonds, and/or through non-covalent interactions, e.g. electrostatic interactions, Van der Waals forces, among other intermolecular interactions.

According to another aspect, the present disclosure relates to a method of preparing the nanotherapeutic, wherein the magnetic resonance imaging moiety is present as the imaging agent. The method involves (i) incorporating the magnetic resonance imaging moiety into the hierarchical silica composite by a method selected from the group consisting of wet impregnation, isomorphous substitution, and enforced impregnation, to form a magnetic hierarchical silica composite, (ii) treating the magnetic hierarchical silica composite at 500-600° C. for 8-16 hours to form a calcined magnetic hierarchical silica composite, (iii) treaing the calcined magnetic hierarchical silica composite with a silanization agent to form a silane coated hierarchical silica composite, (iv) mixing the silane coated hierarchical silica composite with a solution of the antitumor agent forms the nanotherapeutic.

The term "silicalite" refers to a silicate form of ZSM-5 that contains no aluminum in the framework.

The term "bottom-up methodology" used herein refers to a construction approach relying on the self-driven assembly of building blocks into desired structures in an additive fashion to build up a material.

The term "top-down methodology" used herein refers to a fabrication approach relying on adding desired features to a structure by removing elements in a subtractive fashion to manufacture a material. Typical "top-down methodology" includes, but is not limited to lithography, embossing and scanning tip methods.

In some embodiments, the hierarchical silica composite is prepared by using silicalite with particle sizes in the range of 1-5 nm, 1.5-4.5 nm, 2-4 nm or 2.5-3.5 nm as a precursor.

In some embodiments, the silicalite is synthesized using a silica source, e.g. colloidal silica, and a template, e.g. a quaternary ammonium salt, by self-assembly formation through a bottom-up methodology, as disclosed in patent application titled "Hierarchical Siliceous Mesosilicalite Nanocarrier" (application Ser. No. 15/478,794—incorporated herein by reference). The molar ratio of the silica source to the template may be in the range of 100:1 to 1:1, preferably 50:1 to 2:1, more preferably 10:1 to 5:1.

The colloidal silica may be LUDOX® colloidal silica, e.g. LUDOX® AS-30 (W.R. Grace & Co.), LUDOX® AS-40 (W.R. Grace & Co.), LUDOX® AM (W.R. Grace & Co.), LUDOX® ox HS-40 (W.R. Grace & Co.), LUDOX® TM-40 (W.R. Grace & Co.), and LUDOX® LS (W.R. Grace & Co.). Preferably, the colloidal silica is LUDOX® AS-40 (W.R. Grace & Co.).

In some embodiments, the template is a quaternary ammonium halide, e.g. tetraethylammonium bromide, tetrabutylammonium bromide, tetrapropylammonium bromide, tetrapentylammonium bromide. In another embodiment, the template is a quaternary ammonium hydroxide, e.g. tetraethylammonium hydroxide, tetrabutylammonium hydroxide, tetrapropylammonium hydroxide, and tetrapentylammonium hydroxide.

The term "hydrothermal techniques" refers to various techniques of crystallizing substances from high-temperature aqueous solutions at high vapor pressures.

In some embodiments, the hierarchical silica composite is generated from the silicalite using a mesoporous template, e.g. a quaternary ammonium salt, by hydrothermal techniques through a top-down methodology, as disclosed in patent application titled "Hierarchical Siliceous Mesosilicalite Nanocarrier" (application Ser. No. 15/478,794—incorporated herein by reference). The molar ratio of the silicalite to the mesoporous template may be in the range of 100:1 to 1:1, preferably 50:1 to 2:1, more preferably 10:1 to 4:1.

In some embodiments, the mesoporous template is a quaternary ammonium halide, e.g cetyltrimethylammonium bromide, cetyltriethylammonium bromide, dodecyltrimethylammonium bromide, and/or dodecyltriethylammonium bromide. In another embodiment, the mesoporous template is Pluronic F127 (BASF), Pluronic P123 (BASF), Brij-56 (Croda International PLC), and/or Brij-30 (Croda International PLC).

In some embodiments, the resulting hierarchical silica composite is composed of both uniformly-sized mesopores and micropores, which can lead to improved adsorption and sustained release of materials into and out of the composite.

The surface area and pore size of the hierarchical silica composite may be determined by $N_2$ adsorption-desorption isotherms. The size distribution profile may be obtained by the analysis of desorption portion of the isotherms using the Barrett-Joyner-Halenda (BJH) method.

The term "impregnation" used herein refers to a process of incorporating a substance into a support material. The term "wet impregnation" further refers to an incorporation process executed by contacting a solution of the substance with a support material.

In some embodiments, incorporating the magnetic resonance imaging moiety into the hierarchical silica composite involves at least the following: i) mixing the magnetic resonance imaging moiety with the hierarchical silica composite in a solvent at temperatures in the range of 4-60° C., preferably 10-40° C., more preferably 20-30° C. to form a magnetic hierarchical material solution through wet impregnation, ii) removing the solvent in the magnetic hierarchical material solution to form the hierarchical silica composite impregnated with the magnetic resonance moiety.

In some embodiments, removing the solvent is accomplished by heating the magnetic hierarchical material solution at temperatures in the range of 25-200° C., preferably 60-150° C., more preferably 80-100° C. for a period of 4-48 hours, preferably 6-36 hours, more preferably 8-24 hours.

In another embodiment, the hierarchical silica composite is impregnated with the magnetic resonance imaging moiety by incorporating the magnetic resonance imaging moiety through isomorphous substitution, and/or enforced impregnation.

The term "isomorphous substitution" refers to a process of replacing one atom by another in a crystal structure.

The term "enforced impregnation" refers to the wet impregnation process executed under pressures in the range of 5-700 mmHg, 50-500 mmHg, 100-400 mmHg, or 200-300 mmHg.

In a further embodiment of the method, the incorporation of the magnetic resonance imaging moiety into the hierarchical silica composite is evaluated by a Fourier-transform infrared (FT-IR) spectroscopy, X-ray diffraction (XRD) analysis, scanning electron microscopy (SEM), transmission electron microscopy (TEM), magnetic hysteresis analysis, zero-field cooling (ZFC) measurement, and/or field-cooling (FC) measurement.

The term "silanization" used herein refers to a method of surface modification by reacting a surface of silanol groups with alkoxysilane molecules upon hydrolysis followed by condensation reactions to form a silane coating on the surface.

The silanization agent may be a trialkoxyaminosilane, e.g. 3-aminopropyltrimethoxysilane, 3-aminopropyltriethoxysilane, (3-chloropropyl)trimethoxysilane, 4-aminobutyltriethoxysilane, 4-amino-3,3-dimethylbutyltrimethoxysilane, N-(2-aminoethyl)-3-aminopropyltrimethoxysilane, N-(2-aminoethyl)-3-aminopropyltriethoxysilane, aminophenyltrimethoxysilane, and 3-aminopropyltris(methoxyethoxyethoxy)silane, a dialkoxyaminosilane, e.g. 3-aminopropylmethyldiethoxysilane, and 4-amino-3,3-dimethylbutylmethyldimethoxysilane, a monoalkoxyaminosilane, e.g. 3-aminopropyldimethylethoxysilane, and 1-amino-2-(dimethylethoxysilyl)propane, or mixtures thereof. Preferably, the silanization agent is a trialkoxyaminosilane.

In some embodiments, treating the hierarchical silica composite with the silanization agent involves mixing the hierarchical silica composite with the salinization agent with a molar ratio of hierarchical silica composite to silanization agent in the range of 1:50, 1:25, or 1:10 in a solvent under temperatures in the range of 0-50° C., preferably 10-35° C., more preferably 20-28° C. In some embodiments, the silanization agent is pre-dissolved in a solution with a concentration in the range of 0.5-25 w.t. %, preferably 2.5-15 w.t. %, more preferably 5-10 w.t. %.

In some embodiments, a solution of the antitumor agent is mixed with the hierarchical silica composite to load the antitumor agent into the mesopores and micropores of the hierarchical silica composite.

In some embodiments, the solution of the antitumor agent is formed by dissolving the antitumor agent in a solvent with a concentration in the range of 0.1-15 mg/mL, 0.25-12.5 mg/mL, 0.5-10 mg/mL, 1-7.5 mg/mL, or 2-5 mg/mL.

The solvent used herein includes, but is not limited to: organic solvents, e.g. alcohols such as methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol,3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, and cyclohexanol, amide solvents such as dimethylformamide, dimethylacetamide, and N-methyl-2-pyrrolidone, aromatic solvents such as benzene, o-xylene, m-xylene, p-xylene, and mixtures of xylenes, toluene, mesitylene, anisole, 1,2-dimethoxybenzene, α,α,α,-trifluoromethylbenzene, and fluorobenzene, chlorinated solvents such as chlorobenzene, dichloromethane, 1,2-dichloroethane, 1,1-dichloroethane, and chloroform, ester solvents such as ethyl acetate, and propyl acetate, ethers such as diethyl ether, tetrahydrofuran, 1,4-dioxane, tetrahydropyran, t-butyl methyl ether, cyclopentyl methyl ether, and di-isopropyl ether, glycol ethers such as 1,2-dimethoxyethane, diglyme, and triglyme, acetonitrile, propionitrile, butyronitrile, benzonitrile, dimethyl sulfoxide, water, e.g. tap water, distilled water, doubly distilled water, deionized water, and deionized distilled water, and mixtures thereof.

In some embodiments, mixing the hierarchical silica composite with a solution of the antitumor agent involves shaking/stirring throughout the duration of the mixing for about 1-48 hours, preferably 8-36 hours, more preferably 12-24 hours by utilizing a rotary shaker, an overhead magnetic stirrer, or a mechanical stirrer. In another embodiment, mixing the hierarchical silica composite with a solution of the antitumor agent involves mixing in a centrifugal mixer with a rotational speed of at least 600 rpm, preferably 900 rpm, more preferably 1,200 rpm. In one embodiment, mixing the hierarchical silica composite with a solution of the antitumor agent involves sonication.

In a further embodiment of the method, the amount of the antitumor agent loaded into the hierarchical silica composite is determined by a UV-vis spectrophotometer, a Fourier-transform infrared (FT-IR) spectrometer, a high-performance liquid chromatography (HPLC), a nuclear magnetic resonance (NMR) spectroscopy, and/or a thermogravimetric analysis (TGA) method.

In some embodiments, wherein the fluorophore is present as the imaging agent, preparing the nanotherapeutic involves at least the following: (i) treating the hierarchical silica composite with a silanization agent to form a silane coated hierarchical silica composite, ii) mixing the silane coated hierarchical silica composite with a solution of the fluorophore to form a fluorescent hierarchical silica composite, iii) mixing the fluorescent hierarchical silica composite with a solution of the antitumor agent forms the nanotherapeutic.

In some embodiments, treating the hierarchical silica composite with the silanization agent forms a modified surface of a coating of aminoalkyl groups on the hierarchical silica composite. The coating of aminoalkyl groups may further react with the fluorophore. In a preferred embodiment, the fluorophore is rhodamine B isothiocyanate.

In a further embodiment of the method, the amount of the fluorophore incorporated to the hierarchical silica composite is determined by a UV-vis spectrophotometer, a Fourier-transform infrared (FT-IR) spectrometer, a nuclear magnetic resonance (NMR) spectroscopy, a fluorescence spectrophotometer, a confocal laser scanning microscope, and/or a thermogravimetric analysis (TGA) method.

In some embodiments, wherein the magnetic resonance imaging moiety and the fluorophore are present as the imaging agent, preparation of the nanotherapeutic is modified as following: (i) incorporating the magnetic resonance imaging moiety into the hierarchical silica composite by a method selected from the group consisting of wet impregnation, isomorphous substitution, and enforced impregnation, to form a magnetic hierarchical silica composite, (ii) treating the magnetic hierarchical silica composite at 500-600° C. for 8-16 hours to form a calcined magnetic hierarchical silica composite, (iii) treating the calcined magnetic hierarchical silica composite with a silanization agent to form a silane coated hierarchical silica composite, (iv) mixing the silane coated hierarchical silica composite with a solution of the fluorophore to form a fluorescent hierarchical silica composite, (v) mixing the fluorescent hierarchical silica composite with a solution of the antitumor agent forms the nanotherapeutic.

According to another aspect, the present disclosure relates to a method of treating a cancerous tissue located in a subject in need of treatment for cancer. The presently disclosed treatment method includes administering a therapeutically effective amount of the nanotherapeutic to the subject, imaging a location of the nanotherapeutic relative to the cancerous tissue by illuminating the cancerous tissue at an electromagnetic wavelength (excitation wavelength) and detecting a fluorescence signal (emission wavelength), and/or applying an external magnetic field to the subject for magnetic resonance imaging (MRI).

In some embodiments of the method, wherein the fluorophore is present as the imaging agent, the location of the nanotherapeutic is imaged by the illuminating using fluorescence microscopy, confocal laser scanning microscopy, in vivo fluorescence imaging systems, and/or flow cytometry with excitation and emission wavelengths suitable for the fluorophore.

In a further embodiment of the method, the fluorophore typically has a suitable excitation wavelength within the region of 200-1,500 nm, 300-1,000 nm, 400-800 nm, or 500-700 nm, and a suitable emission wavelength within the region of 200-1,500 nm, 300-1,000 nm, 400-800 nm, or 500-700 nm.

In some embodiments of the method, wherein the magnetic resonance imaging moiety is present as the imaging agent, the location of the nanotherapeutic is imaged by collecting MR images using a clinical MRI instrument.

In some embodiments, the location of the nanotherapeutic is imaged by performing a T2 weighted MR image acquirement with a head coil on a MR scanner with a magnet field strength of at least 1.5 tesla, preferably at least 3 tesla, more preferably at least 6 tesla. In one embodiment, T2 weighted MR image acquirement is performed by applying a T2-weighted spin-echo pulse sequence with proper repetition time (TR), echo time (TE) and number of scans.

In some embodiments of the method, wherein the magnetic resonance imaging moiety is present, an external magnetic field is applied to remotely propel and deliver the nanotherapeutic towards the cancerous tissue. In some embodiments, the external magnetic field has a field strength applied at the site of cancerous tissue in need of treatment for cancer within the order of 100-2000 mT, 150-1500 mT, 200-1000 mT, or 300-800 mT, depending on competing forces within the subject exerted on the nanotherapeutic.

In some embodiments of the method, in vitro release profile of the antitumor agent from the nanotherapeutic is evaluated using a UV-vis spectrophotometer after dispersing the nanotherapeutic in a solution at temperatures in the range of 18-50° C., preferably 25-45° C., more preferably 30-40° C. In one embodiment, the in vitro release profile of the antitumor agent from the nanotherapeutic is evaluated using a UV-vis spectrophotometer after dispersing the nanotherapeutic in a phosphate buffered saline (PBS) solution at 37° C. in an incubator at predetermined time intervals in the range of 1/60-48 hours, 5/60-42 hours, 0.5-36 hours, 1-30 hours, 2-24 hours, 4-18 hours, or 8-12 hours.

The dispersion of the nanotherapeutic may be characterized by dynamic light scattering (DLS), and/or ζ-potential measurement.

In some embodiments, the effectiveness of the nanotherapeutic against cancer cells is assessed by its $IC_{50}$ values, $EC_{50}$ values, apoptotic effects and/or therapeutic index. Preferably, the effectiveness of the nanotherapeutic is assessed by its $IC_{50}$ values and apoptotic effects.

In some embodiments, the cancer cells are derived from human cancer cell lines, including, but are not limited to liver cancer cell lines, e.g. Hep 3B, Hep G2, and SK-HEP-1, lung cancer cell lines, e.g. A549, SHP-77, and NCI-H69/LX20, skin cancer cell lines, e.g. C32TG, A375, and MCC26, breast cancer cell lines, e.g. MDA-MB-231, MCF7, and VP303. In a preferred embodiment, the cancer cells are human Hep G2 cell line. In other embodiments, the cancer cells are collected from a human patient who is at risk of having, is suspected of having, has been diagnosed with, or is being monitored for recurrence of at least one type of cancer, preferably liver cancer.

In vitro $IC_{50}$ values may be determined by cell viability assay methods such as ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. Preferably, a trypan blue assay and/or a MTT assay are used.

In vitro apoptotic effects of the nanotherapeutic may be studied by methods including, but not limited to DNA fragmentation analysis by electrophoresis, RNA analysis by qPCR, fluorescent microscopy, and western blotting analysis.

In most embodiments, the method further comprises detecting a mutation in a cancer biomarker and/or measuring a concentration level of a cancer biomarker before and after the nanotherapeutic is administered to the subject. The term "biomarker" refers to a characteristic that is objectively measured and evaluated as an indicator of normal biological processes, pathogenic processes, or pharmacologic responses to a therapeutic intervention. The term "cancer biomarker" used herein refers to a substance secreted by a tumor or a process that is indicative of the presence of cancer in the body. Examples of cancer biomarkers include, but are not limited to HER2, BRCA1, BRCA2, Alpha-fetoprotein (AFP), AFP-L3, DCP, CYFRA 21-1, EGFR (HER1), KRAS gene, and BRAF V600. Cancer biomarkers may be indicative of a response towards a treatment. Examples of these indicative cancer biomarkers include, without limitation, AFP, AFP-L3, and DCP for liver cancer.

The mutation in the cancer biomarker may be detected by procedures such as, without limitation, restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA).

The concentration level of the cancer biomarker may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. Preferably, Western blotting is used.

The term "Western blotting" used herein refers to a method to detect the presence and measure the concentration of a biomarker in a sample.

The term "sample" used herein refers to any biological sample obtained from the subject in need of treatment for cancer including a single cell, multiple cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

In vivo $IC_{50}$ values and apoptotic effects of the nanotherapeutic may be studied on an animal model by methods described herein. Preferably, mouse of BL6 strain is used as the animal model.

In vivo distribution of the nanotherapeutic in the animal model may be monitored and analyzed by an in vivo imaging system, e.g. IVIS™ Spectrum In Vivo Imaging System (PerkinElmer, Inc.), and a magnetic resonance imaging (MRI) instrument with a magnetic field strength in the range of 5-20 tesla, preferably 8-15 tesla, more preferably 11-12.5 tesla.

In some embodiments, administering a therapeutically effective amount of the nanotherapeutic involves administering the nanotherapeutic or the solvate thereof in an effective amount in a range of 1-500 mg/kg based on the weight of the subject, preferably 100-400 mg/kg, more preferably 200-300 mg/kg, based on the loading capacity of the antitumor agent of the nanotherapeutic.

In some embodiments, a formulation of the nanotherapeutic or the solvate thereof has a composition in the form of solid, semi-solid or liquid forms, such as powders, liquids, lyophilized forms, suspensions, tablets, pills, capsules, creams, ointments, gels, pastes, and transdermal patches.

The terms "administer", "administration", and the like, as used herein, refer to methods that may be applied to enable delivery of an active ingredient and/or composition to a subject. These methods used herein include, but are not limited to, oral routes, parenteral injection such as intravenous, intramuscular, subcutaneous, and infusion, topical application, and rectal administration. In preferred embodiments, the nanotherapeutic and/or the nanotherapeutic formulation described herein are administered intravenously.

In some embodiments, the nanotherapeutic and/or the nanotherapeutic formulation are administered at various dosages (e.g. an initial dose with an effective amount of 400 mg/kg and a subsequent dose with an effective amount of 200 mg/kg). In some embodiments, the interval between the administration of the composition and a subsequent administration is about 1-30 minutes, 30-60 minutes, 1-2 hours, 2-6 hours, 2-12 hours, 12-24 hours, 1-2 days, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 1 moth, 2 months, 3 moths, 4 months, 5 months, 6 months, 7 months, 8 months, 9 months, 10 months, 11 months, 12 months, 1 year, 2 years, or any period of time in between. Preferably, the composition is administered once every week for at least 2 weeks, 4 weeks, 5 weeks, 6 weeks, 7 weeks or 8 weeks. In certain embodiments, the composition and a subsequent composition are administered less than 1 day, 1 week, 2 weeks, 3 weeks, 1 month, 2 months, 3 months, 6 months, 1 year, 2 years, or 5 years apart.

In some embodiments, the composition has different release rates categorized as immediate release and sustained release.

The term "immediate release" refers to the release of a substantial amount of an active ingredient immediately upon administration. Typically, an immediate release indicates a complete (100%) or less than complete (e.g. about 70% or more, about 80% or more, about 90% or more, about 95% or more, about 99% or more, or 99.9%) dissolution of an active ingredient within 1-60 minutes, 1-30 minutes, or 1-15 minutes after administration.

The term "sustained release" refers to the release of an active ingredient from a composition and/or formulation over an extended period of time. In some embodiments, a sustained release indicates a dissolution of an active ingredient over a period of time up to 30 minutes, 60 minutes, 3 hours, 12 hours, 24 hours upon administration. In preferred embodiments, the nanotherapeutic and/or the nanotherapeutic formulation described herein have a sustained release.

In some embodiments, imaging a location of the nanotherapeutic relative to the cancerous tissue by illuminating the cancerous tissue at an electromagnetic wavelength (excitation wavelength) and detecting a fluorescence signal (emission wavelength), and/or applying an external magnetic field to the subject for magnetic resonance imaging (MRI) are executed during and after administration. In some embodiments, imaging a location of the nanotherapeutic is conducted over a period of time up to 5 minutes, 30 minutes, 60 minutes, 3 hours, 12 hours, 24 hours, 48 hours, 1 week, 4 weeks, 3 months, 6 months, or 1 year upon administration of nanotherapeutic and/or the nanotherapeutic formulation.

According to another aspect, the present disclosure relates to an oxidative dehydrogenation catalyst having a hierarchical silica composite and an active catalytic material impregnated on the hierarchical silica composite.

The hierarchical silica composite may include a stereoregular MCM-41 ordered arrangement of uniformly-sized mesopores with diameters in a range of 2-50 nm, 3-10 nm, or 4-5 nm, and mesopore walls having a thickness of about 1 to about 5 nm, about 2 to about 4 nm, or about 3 to about 4.5 nm, and a stereoregular ZSM-5 silicalite ordered arrangement of micropores with diameters of 0.1-1.99 nm, 0.2-1 nm, or 0.3-0.7 nm located within the mesopore walls.

The active catalytic material may include nickel and/or nickel oxide, and at least one cation dopant selected from the group consisting of $Nb^{5+}$, $Al^{3+}$, $Ti^{4+}$, $Ta^{5+}$, $Bi^{5+}$, and/or oxides thereof.

The catalyst disclosed herein may be prepared by a process including at least the following steps. In a first step, mixing a dispersed nickel species with the hierarchical silica composite to form a Ni impregnated hierarchical silica composite. The nickel species can be incorporated into the mixing step in the form of pure metallic elements, as salts, e.g. sulfates, nitrates, and halides, as oxides, as hydroxides, as alkoxides, or as mixtures thereof.

In some embodiments, elements Nb, Al, Ti, Ta, Bi, and mixtures thereof are introduced as higher valence cation dopants into the mixing step in the form of pure metallic elements, as salts, as oxides, as hydroxides, as alkoxides, or as mixtures thereof.

The metal elements described above may be mixed as the active catalytic material with the hierarchical silica composite to form a solution or slurry, which is subsequently stirred or left to stand. In one embodiment, the stirring is carried out by utilizing a rotary shaker, a magnetic stirrer, or an overhead mechanical stirrer, at temperatures in the range of 100-250° C., preferably 150-200° C. for a time period in the range of 8-48 hours, 12-36 hours, or 16-24 hours. In another embodiment, the solution or slurry is sonicated.

The resulting mixture may be collected as a precipitate and washed by a solvent. Preferably the solvent is de-ionized water.

The resulting washed precipitate may be further dried. Drying may be executed by evaporation by stirring, evaporation by a rotavapor, vacuum drying, spray drying, among other methods. A preferred drying process is evaporation by stirring in air at temperature range of 60-200° C., preferably 80-180° C., more preferably 100-160° C., for 8-48 hours, 12-36 hours, or 16-32 hours to form a dried precipitate.

The dried precipitate may be further calcined. Calcination of the dried precipitate may be carried out in a gas atmosphere, e.g. nitrogen, helium, argon, air, or mixtures thereof. The gas atmosphere can be created by a flow of gas or maintained by a static gas. Calcination temperature may be at 300-1,000° C., preferably 400-800° C., more preferably 500-600° C. Calcination time period may range from 1-48 hours, 4-24 hours, or 8-16 hours. Calcination process may be carried out in a furnace, a kiln, or a reactor. A preferred calcination process is conducted in a muffle furnace in a static air atmosphere at 400-800° C., more preferably 500-600° C. for 8-16 hours to form the calcined catalyst.

In some embodiments, the calcined catalyst described above is further pelletized. The pelletizing process may be conducted by utilizing a pelletizing system by compressing the calcined catalyst of 50-250 mg, 100-200 mg, or 125-175 mg to form a catalyst tablet.

In some embodiments, the resulting catalyst tablet is crushed to form the catalyst for oxidative dehydrogenation. The crushing process may be carried out by utilizing a grinding method, e.g. drying milling, wet milling, and cryogenic milling, to form the catalyst for oxidative dehydrogenation. Preferably, the catalyst has particles with sizes ranging from 0.1-2 mm, preferably 0.2-1.2 mm, more preferably 0.3-0.8 mm in diameter. In one embodiment, the particles are further sieved.

In some embodiments, the oxidative dehydrogenation catalyst has about 10-99.9 w.t. %, 10-90 w.t. %, 10-80 w.t. %, 10-70 w.t. %, 10-60 w.t. %, 10-50 w.t. %, 10-40 w.t. %, 10-30 w.t. %, or 10-20 w.t. % of the active catalytic material, and the rest being the hierarchical silica composite.

In some embodiments of the method, the catalyst disclosed herein is characterized by Fourier-transform infrared (FT-IR) spectroscopy, scanning electron microscopy (SEM), transmission electron microscopy (TEM), atomic absorption spectroscopy, powder X-ray diffraction, diffuse reflectance UV-vis spectroscopy, X-ray absorption spectroscopy, transmission Mossbauer spectroscopy, $N_2$ adsorption manometry, thermogravimetric-differential thermal analysis.

According to another aspect, the present disclosure relates to a method of oxidatively dehydrogenating an alkane to form an olefin. The presently described oxidative dehydrogenation method involves contacting the alkane with the catalyst disclosed herein, an oxidant, and an inert gas in a reactor to convert the alkane to the olefin. As disclosed previously, the catalyst may include a hierarchical silica composite and an active catalytic material impregnated on the hierarchical silica composite. The active catalytic material has nickel and/or nickel oxide, and at least one cation dopant selected from the group consisting of $Nb^{5+}$, $Al^{3+}$, $Ti^{4+}$, $Ta^{5+}$, $Bi^{5+}$, and/or oxides thereof.

In some embodiments, the catalyst is loaded into a reactor, e.g. a fixed-bed reactor, a fluidized-bed reactor, and a micro-channel reactor. Preferably, the catalyst is loaded into a fixed-bed stainless steel tube reactor.

In some embodiments of the method, the alkane contains ethane, recycled ethane recovered from the reactor, and/or mixtures thereof.

In some embodiments of the method, the oxidant includes $O_2$, air, and/or mixtures thereof.

The oxidant may be mixed with a co-feed gas. Preferably, the co-feed gas is $CO_2$. Oxidative dehydrogenation in the presence of $CO_2$ as a co-feed gas is considered safe, energy efficient and ecofriendly.

In some embodiments, an inert gas, e.g. hydrogen, nitrogen, helium, argon, and/or mixtures thereof, is introduced to the reactor and mixed with the oxidant. Preferably, the inert gas is helium.

A typical composition molar ratio of alkane to oxygen for oxidative dehydrogenation method disclosed herein may be about 1:1, 1:10, 1:25, or 1:100.

A typical molar ratio of the oxidant to the co-feed gas may be within the range of 0.1:1, 1:1, 2.5:1, 5:1, 10:1, 50:1 or 100:1.

A typical molar ratio of the oxidant to the inert gas may be within the range of 0.01:1, 0.1:1, 1:1, 2.5:1, 5:1, or 10:1.

The reactor temperature may be in the range of 300-800° C., preferably 400-700° C., more preferably 500-600° C. The reactor pressure may be in the range of 70-130 kPa, preferably 80-120 kPa, more preferably 90-110 kPa.

In some embodiments, the method involves flowing the alkane through the reactor at a flow rate of 0.1-10 mmol $min^{-1}$, preferably 0.25-5 mmol $min^{-1}$, more preferably 0.5-1 mmol $min^{-1}$ through the reactor. The method further involves flowing the inert gas through the reactor at a flow rate of 10-200 mL $min^{-1}$, 50-150 mL $min^{-1}$, more preferably 75-125 mL $min^{-1}$.

In some embodiments, the method further involves pretreating the catalyst with the inert gas at an inert gas flow rate of 10-200 mL $min^{-1}$, 50-150 mL $min^{-1}$, or 75-125 mL $min^{-1}$, and a temperature of 400-700° C., 450-650° C., or 500-600° C. for a period of 0.25-2 hours, 0.5-1.5 hours, or 0.75-1.25 hours.

The catalytic oxidative dehydrogenation disclosed herein may have a reaction time in the range of 0.1-10 hours, preferably 0.5-7.5 hours, more preferably 1-5 hours. A typical reaction conversion may be in the range of 20-29.9%, 30-39.9%, 40-49.9%, 50-59.9%, 60-69.9%, 70-79.9%, 80-89.9%, or 90-99.9% ethane conversion. A typical reaction yield may be in the range of 20-29.9%, 30-39.9%, 40-49.9%, 50-59.9%, 60-69.9%, 70-79.9%, 80-89.9%, or 90-99.9% ethylene yield.

In a further embodiment of the method, oxidative dehydrogenation reaction products are analyzed by a gas chromatograph. Preferably, the gas chromatograph is equipped with FID using a HP-INNOWAX® polyethylene glycol stationary phase gas chromatograph column. In a further embodiment, analysis of gaseous products (CO, $CO_2$, and $H_2$) is performed with a gas chromatograph. Preferably, the gas chromatograph has a packed Molecular Sieve-5A column and PORAPAK® Q polymer packing.

The examples below are intended to further illustrate protocols for synthesizing and testing the nanotherapeutic, as well as preparing and characterizing the oxidative dehydrogenation catalyst, and uses thereof, and are not intended to limit the scope of the claims.

Example 1: Nanotherapeutic

Synthesis

The mesoporous silicalite with ordered and disordered hexagonal pores was synthesized through top-down approach using nanozeolitic seed and mesoporous templates such as CTAB, and F127. The parent silicalite was dissolved using various molar concentration of NaOH, and then pH was adjusted using diluted sulfuric acid. The material was left for hydrothermal ageing for few days and then collected through filtration, drying and calcination steps. The obtained nanomaterials were further modified using various types of silanes such as aminopropyltriethoxysilane, 3-aminopropyltrimethoxysilane, 3-chloropropyl trimethoxysilane by dispersing in a toluene solution. The silane was added and refluxed for 6 h. The solution was centrifuged, washed and dried.

Drug Loading and Release

Cisplatin drug loading was carried out using a certain proportion of the cisplatin solution with a support solution (2 mL/drug or support) by stirring at room temperature for 24 h. Then phosphate buffered saline (PBS) solutions at different pH levels were prepared for drug release testing. The cisplatin loaded mesoporous samples were dispersed at 37° C. in the incubator mimicking body temperature conditions. At different time intervals, the suspension was centrifuged and the quantity of drug released was evaluated using a UV-Vis spectrophotometer.

In Vitro Study (i) Experimental Design

Group I: Hep G2 cell line

Group II: Hep G2 cell line+Cisplatin

Group III: Hep G2+modified iron hierarchical silica

Group IV: Hep G2 cell line+Cisplatin loaded modified iron hierarchical silica (ii) Hep G2 Cell Line Cell Culture Hep G2 was used for the cell culture. The cells were re-suspended in Dulbecco's Modified Eagle's medium (DMEM) with 15% heat inactivated fetal calf serum and 3% penicillin-streptomycin.

(iii) Cell Viability Determination by Trypan Blue Staining

Trypan blue was used for cell counting. PBS was added to 0.4% Trypan blue for cell counting. 0.2 mL of tryponised cell solution was placed in 0.3 mL of medium and mixed with 0.5 mL of 0.4% trypan blue. A hemocytometer was then used for cell counting. The number of cells without trypan blue was counted as viable cells. The cell viability is calculated using the following equation:

$$\text{Percentage of viability} = \frac{\text{Number of unstained cells}}{\text{Number of stained cells}} \times 100$$

(iv) Cell Proliferation Assay MTT

The MTT assay was carried out to determine the cell proliferation by a method described by Mosmann (Mosmann T. J *Immunol. Methods* 1983, 65, 55, incorporated herein by reference). 10 μL of MTT solution (5 mg/mL in PBS) was added to each well. Aluminum foil was used to wrap the MTT plates. The plates was then incubated for 4 hours at 37° C. 180 μL DMSO was added to each well after incubation and then the plates were kept in the dark overnight. A microplate reader was used to measure the absorbance at wavelength of 570 nm. The average absorbance in cells treated with drug was compared to the control in order to determine the percentage of viable cells. This study was carried out in different concentrations for different time periods by fixing the drug dose and treatment time.

(v) Molecular Studies: Apoptotic Effect of the Nanotherapeutic (DNA Fragmentation Analysis by Agarose Gel Electrophoresis)

Yokozawa and Dong method of Agarose gel electrophoresis (Yokozawa T.; Dong E. *Nephron.* 2001, 89, 433, incorporated herein by reference) was used for DNA analysis. DNA was isolated as per manufacturer's instructions and then dissolved in Tris/Borate/EDTA (TBE) Buffer. 1 mg of DNA sample was electrophoresed on a 1.2% Agarose gel using TBE buffer for 3 hours at 40 V. Ethidium bromide (EtBr) was then used to stain the gel. The gel was finally examined under a UV transilluminator and then photographed.

(vi) RNA Isolation, cDNA Synthesis, and qPCR

RNA was isolated from the treated and control Hep G2 cells by Rnase plus Micro and Mini Kit (Qiagen). RNA was measured by a Qubit 3.0 Fluorometer (Thermo Fisher). cDNAs was generated from the isolated RNA by QuantiTect Reverse Transcription Kit (Qiagen). Gene expression of Bax Bcl2, Cytochrome C, p53 and caspase 9 was analyzed by a 7500 Fast Real-Time PCR System (Applied Biosystems) using QUANTINOVA® SYBR GREEN© (Qiagen) PCR probe-based real-time quantitative Polymerase Chain Reaction kit. Gene expression was calculated and normalized to a house keeping gene, GAPDH.

(vii) Fluorescent Microscope Analysis

Nuclear morphological changes of apoptotic cells was examined after staining using Hoechst 33342 (Invitrogen) at room temperature for 10 minutes (in dark area). Briefly, treated cells was fixed by 4% paraformaldehyde for 30 minutes and washed with PBS for three times. Apoptosis was assessed by counting the apoptotic cells under fluorescence microscope detected by shrunken nuclei and condensed chromatin.

(viii) Western Blotting Analysis

Nanotherapeutic treated cells and control cells were lysed by a cold RIPA buffer (50 mM HEPES, 150 mM NaCl, 0.125 mM EDTA, 0.1% SDS, 0.1% TWEEN®-20 (non-ionic surfactant and emulsifier), and 0.5% sodium deoxycholate). Fresh protease inhibitor cocktail (Roche) together with 1 mM dithiothreitol (DTT) was added directly to lysis buffer before using. Cell pellet was homogenized for 30 minutes over an ice-bath. Lysates were centrifuged at 120,000 rpm for 10 minutes before collecting the supernatant. Total protein concentration was measured by BCA protein assay (Thermo Fisher). 60 μg of protein per sample was prepared, loaded on SDS polyacrylamide gels, and transferred to PVDF membranes. The blots were blocked with 5% skimmed milk or blocking buffer (biorad) in PBS containing 0.1% TWEEN®-20 (PBST) for 1 hour at room temperature. Membranes incubated overnight with primary antibodies against Bax, Bcl-2, cytochrome C, p53, and R-actin were used as a loading control, caspase activated cleaved forms were assessed by caspase-3, caspase-7, and caspase-9 blotting.

Next day, the membranes were washed with PBST three times for 30 minutes each, and incubated with horseradish peroxide conjugated secondary antibody for 1 hour at room temperature. The bands were developed by ESL substrate (biorad) and visualized by MOLECULAR IMAGER® Gel Doc™ gel imaging and documentation system (biorad).

In Vivo Study and Tumor Imaging

Hep G2 cells were treated with fluorescent dye and hierarchical silicalite nanoparticles. After fixation with either 4% paraformaldehyde or cold methanol for 30 min, cells were permeabilized by 0.5% TRITON™ X-100 (non-ionic surfactant) in PBS for 10 min, and blocked with 0.3% goat serum-PBS (blocking buffer). To detect subcellular localization of nanoparticles, primary antibodies (Abs) against various cellular organelle markers, such as nuclear envelope, endoplasmic reticulum, Golgi apparatus, P/GW-bodies, stress granules, endosomes, lysosomes, and plasma membrane were selected. The Abs diluted in blocking buffer were incubated overnight. Next day, unbound Abs were washed and incubated with appreciate fluorescent-conjugated secondary Abs dye for 1 hour. Cells were mounted with fluorescent mounting medium PROLONG DIAMOND®, SLOWFADE DIAMOND© (Thermo Fisher anti-fade mountant). Images of the designed nanoparticles were visualized with LSM780®/ELYRA PS.1® Confocal Laser Scanning System (Carl Zeiss Inc.). This microscopy system was equipped with an inverted AXIO OBSERVER© Z.1 microscope, a confocal module with 34 spectral detection channels via 32-Ch GaAsP detectors plus 2 PMTs, 4 lasers (diode 405 nm, solid-state laser 561 nm, HeNe 633 nm, and multi-line Ar 458/488/514 nm), wide assortment of high quality objectives with both short and long working distances, a piezo scanning stage for advanced tiling capabilities. This microscopy system also had a super-resolution module ELYRA PS.1® equipped with 4 lasers (diode 405 nm, solid-state 561 nm, solid-state 488 nm, and solid-state 642 nm), integrated two methods of super-resolution into one, a turn-key platform, a super-resolution structured illumination microscopy (SR-SIM) and a photoactivated localization microscopy/direct stochastic optical reconstruction microscopy (PALM/STORM), 2 deep cooling EMCCD cameras dedicated super-resolution registration. Imaging analysis was performed by ZEN© software (2012 64 bit version).

After collecting all data sets from in vitro cell-based study, we applied similar methods to in vivo study on the nanotherapeutic to assess whether the drug delivery system is useful for diagnosis. Commonly available mouse BL6 strain was used as the animal model. After being administrated into mice, the nanotherapeutic was chased and traced by using IVIS™ spectrum in vivo imaging system (PerkinElmer) under the anesthesia to monitor its delivery into the body. Similar experiments were conducted using an 11.7 T magnetic resonance imaging (MRI). All experiments were performed under the approval from the Animal Research Committee of the Research Institute for Microbial Diseases, Osaka University (Japan).

Example 2: Oxidative Dehydrogenation Catalyst and Methods

Catalyst Synthesis

Silicalite with particle size 1-2 nm was prepared using LUDOX® AS-40 (colloidal silica) and TPABr as the silica and templating agent. The mesosilicalite was prepared using CTAB as the mesotemplating agent through a top-down approach methodology. Silicalite, mesosilicalite, or alumina was used as the catalyst support. Highly dispersed and stable nickel species in support with higher valence cation dopants such as $Nb^{5+}$, $Al^{3+}$, $Ti^{4+}$, $Ta^{5+}$ and $Bi^{5+}$ was impregnated over Silicalite/mesosilicalite/monodispersed silica (80 nm), alumina with stirring. After stirring, the precipitates were filtrated, washed with de-ionized water, dried in air at 110° C. for 24 hours, and calcined at 550° C. for 12 hours in a muffle furnace in a static air atmosphere. After calcination, the catalysts were tested in the oxidative dehydrogenation of ethane.

Catalyst Characterizations

Atomic absorption spectroscopy was used for the determination of metal content in each sample synthesized above. Powder X-ray diffraction was recorded on a RIGAKU® powder diffraction unit. The diffraction pattern was identified by comparing with those included in the JCPDS database (Joint Committee of Powder Diffraction Standards). Diffuse reflectance UV-vis spectroscopic measurements was recorded on a JASCO® UV/VIS/NIR (V-570) spectrophotometer. X-ray absorption spectroscopic measurements were performed at room temperature in the transmission mode at a EXAFS facilities installed at the BL01B1 line of Spring-8

JASRI, Harima, Japan, using a Si(1 1 1) monochrometer. Transmission Mossbauer spectra of pelletized powder samples were recorded at room temperature, using a constant acceleration mode (Topologic System Co.) of a radiation source with about 40 MBq 57Co(Cr) and a YAP scintillation counter. Doppler velocity was calibrated with reference to α-Fe. Thermogravimetric-differential thermal analysis (TG-DTA) of the catalyst was performed under an inert atmosphere of $N_2$ (20 mL $min^{-1}$) with a Shimadzu TGA-50 and DTA-50 analyzers using 50 mg of sample at a rate of 10° C. $min^{-1}$. Temperature programmed reduction (TPR) of the catalyst was performed at a heating rate of 10° C. $min^{-1}$ from ambient temperature to 1100° C. using a mixture of 5 vol. % $H_2$/Ar at a rate of 100 mL $min^{-1}$ as reducing gas, after passing through a 13-molecular sieve trap to remove water. Temperature-programmed oxidation (TPO) of the catalysts was carried out in a U-shaped quartz reactor. 150 mg of the catalyst after the dehydrogenation of ethane at 550° C. for 1 h was used to determine the amount of carbon deposit on the catalyst. $N_2$ adsorption (−196° C.) study was used to examine both BET surface area and the porous property of the mixed metal oxide supporter over Silicalite/mesosilicalite/alumina support.

Catalyst Evaluations

Oxidative dehydrogenation of ethane was conducted using a fixed-bed gas flow reactor at atmospheric pressure. A quartz triple cell tube reactor (inner diameter of 8 mm) was used as a reactor. In oxidative dehydrogenation reactions, typically 0.15-0.3 g of catalyst, which had been pelletized and crushed to the particles 0.3-0.8 mm in diameter, was loaded into the reactor. The catalyst was pre-treated in a nitrogen gas flow (30 mL $min^{-1}$) at 550° C. for 1 h. The reaction was started by introducing a gas mixture of ethane/nitrogen/air with flow of 1.2/18/12 mL/min with $O_2/C_2$ ratio of 2 to the reactor.

The reaction products (ethylene) were analyzed by an on-line gas chromatograph equipped with FID using GC-Gaspro capillary column. The oxygenated products were also analyzed using TCD detector equipped with SHIN CARBON© 80/100 mesh SS column and MS5A 60/80 mesh SS column for gases (nitrogen, oxygen, CO, $CO_2$ and $H_2$).

The invention claimed is:

1. A method of treating a cancerous tissue located in a subject in need of treatment for cancer, comprising:
- administering a therapeutically effective amount of a nanotherapeutic to the subject; and
- imaging a location of the nanotherapeutic relative to the cancerous tissue by
  - illuminating the cancerous tissue at an electromagnetic wavelength and detecting a fluorescence signal; and/or
  - applying an external magnetic field to the subject for magnetic resonance imaging;
- wherein the nanotherapeutic, comprises:
  - an antitumor agent;
  - a fluorophore;
  - a magnetic resonance imaging moiety; and
  - a hierarchical silica composite,
  - wherein the hierarchical silica composite, comprises:
    - a stereoregular MCM-41 ordered arrangement of uniformly-sized mesopores with diameters in a range of 10-50 nm and mesopore walls having a thickness of 3 to about 5 nm; and
    - a stereoregular ZSM-5 ordered arrangement of uniformly-sized micropores with diameters of less than 2 nm located within the mesopore walls of the stereoregular MCM-41; and
    - a silane coating that coats at least a portion of a surface of the hierarchical silica composite,
  - wherein the magnetic resonance imaging moiety is incorporated into a lattice of the hierarchical silica composite by isomorphous substitution,
  - wherein the antitumor agent is located inside the mesopores of the hierarchical silica composite,
  - wherein an amount of the antitumor agent is in a range of 10-20 wt. %,
  - wherein an amount of the hierarchical silica composite is in a range of 15-70 wt. %,
  - wherein an amount of the fluorophore is in a range of 5-7.5 wt. %, and
- wherein an amount of the magnetic resonance imaging moiety is in a range of 15-25 wt. %, all of which are relative to the total weight of the nanotherapeutic.

2. The method of claim 1, wherein the fluorophore is present as an imaging agent, and the location of the nanotherapeutic is imaged by the illuminating.

3. The method of claim 1, wherein the magnetic resonance imaging moiety is present as an imaging agent, and the location of the nanotherapeutic is imaged by the applying.

4. The method of claim 1, wherein an amount of the silane coating is in a range of 1-20 wt. %, relative to the total weight of the hierarchical silica composite in the nanotherapeutic.

5. The method of claim 1, wherein the silane coating has a thickness of 10-200 Å.

6. The method of claim 1, wherein the hierarchical silica composite has a silicon to aluminum molar ratio in a range of 1,000:1 to 3,000:1 in the nanotherapeutic.

7. The method of claim 1, wherein the mesopores in the nanotherapeutic have a pore volume in the range of 0.9-1.5 $cm^3/g$ and a surface area in the range of 1,000-1,600 $m^2/g$.

8. The method of claim 1, wherein the antitumor agent is cisplatin.

9. The method of claim 1, wherein the fluorophore is rhodamine B isothiocyanate.

10. The method of claim 1, wherein the magnetic resonance imaging moiety is iron and/or an oxide thereof.

* * * * *